United States Patent
Peterson et al.

(10) Patent No.: US 10,226,367 B2
(45) Date of Patent: Mar. 12, 2019

(54) APPARATUS AND METHODS FOR FILLING A DRUG ELUTING MEDICAL DEVICE VIA CAPILLARY ACTION

(71) Applicant: Medtronic Vascular, Inc., Santa Rosa, CA (US)

(72) Inventors: Justin Peterson, Santa Rosa, CA (US); James Mitchell, Windsor, CA (US); Abby S. Pandya, Boston, MA (US); Nathanael Glucklich, Santa Rosa, CA (US); Justin Goshgarian, Santa Rosa, CA (US); Rajen Kumar, Santa Rosa, CA (US); Andrew Czyzowski, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 252 days.

(21) Appl. No.: 15/383,065

(22) Filed: Dec. 19, 2016

(65) Prior Publication Data

US 2018/0168834 A1 Jun. 21, 2018

(51) Int. Cl.
*A61M 5/00* (2006.01)
*A61F 2/915* (2013.01)
(Continued)

(52) U.S. Cl.
CPC .............. *A61F 2/915* (2013.01); *A61L 31/16* (2013.01); *A61M 31/002* (2013.01);
(Continued)

(58) Field of Classification Search
CPC ............ A61F 2/915; A61F 2002/91575; A61F 2210/0076; A61F 2210/0014;
(Continued)

(56) References Cited

U.S. PATENT DOCUMENTS

| 4,539,226 A | 9/1985 | Paek et al. |
| 4,886,062 A | 12/1989 | Wiktor |

(Continued)

FOREIGN PATENT DOCUMENTS

| WO | WO2004/091686 | 10/2004 |
| WO | WO2011/008896 | 1/2011 |
| WO | WO2012/036929 | 3/2012 |

OTHER PUBLICATIONS

U.S. Appl. No. 61/244,049, filed Sep. 20, 2009, Thompson et al.
(Continued)

*Primary Examiner* — Jason K Niesz
(74) *Attorney, Agent, or Firm* — Medler Ferro Woodhouse & Mills PLLC

(57) ABSTRACT

Methods and apparatus are disclosed for filling a therapeutic substance or drug within a hollow wire that forms a stent. The stent is placed within a chamber housing a fluid drug formulation. During filling, the chamber is maintained at or near the vapor-liquid equilibrium of the solvent of the fluid drug formulation. To fill the stent, at least a portion of the stent is placed into contact with the fluid drug formulation until a lumenal space defined by the hollow wire is at least partially filled with the fluid drug formulation via capillary action. After filling is complete, the stent is retracted such that the stent is no longer in contact with the fluid drug formulation. The solvent vapor pressure within the chamber is reduced to evaporate a solvent of the fluid drug formulation. A wicking means may control transfer of the fluid drug formulation into the stent.

20 Claims, 21 Drawing Sheets

(51) Int. Cl.
*A61M 31/00* (2006.01)
*A61L 31/16* (2006.01)

(52) U.S. Cl.
CPC .............. *A61F 2002/91558* (2013.01); *A61F 2002/91575* (2013.01); *A61F 2210/0004* (2013.01); *A61F 2210/0014* (2013.01); *A61F 2210/0076* (2013.01); *A61F 2250/0068* (2013.01); *A61L 2420/02* (2013.01); *A61M 2205/04* (2013.01)

(58) Field of Classification Search
CPC .. A61F 2002/91558; A61F 2250/0068; A61M 31/002; A61M 2205/04; A61L 2420/02
See application file for complete search history.

(56) References Cited

U.S. PATENT DOCUMENTS

| | | | |
|---|---|---|---|
| 5,019,090 | A | 5/1991 | Pinchuk |
| 5,133,732 | A | 7/1992 | Wiktor |
| 5,713,949 | A | 2/1998 | Jayaraman |
| 5,782,903 | A | 7/1998 | Wiktor |
| 5,891,507 | A | 4/1999 | Jayaraman |
| 6,136,023 | A | 10/2000 | Boyle |
| 6,203,551 | B1 | 3/2001 | Wu |
| 6,368,658 | B1 | 4/2002 | Schwarz et al. |
| 6,517,889 | B1 | 2/2003 | Jayaraman |
| 6,743,462 | B1 | 6/2004 | Pacetti |
| 7,563,324 | B1 | 7/2009 | Chen et al. |
| 7,901,726 | B2 | 3/2011 | McMorrow et al. |
| 8,291,854 | B2 | 10/2012 | Behnisch et al. |
| 8,381,774 | B2 | 2/2013 | Mitchell et al. |
| 8,518,490 | B2 | 8/2013 | Ito et al. |
| 8,668,732 | B2 | 3/2014 | Scheuermann et al. |
| 8,828,474 | B2 | 9/2014 | Mitchell et al. |
| 8,840,660 | B2 | 9/2014 | Weber |
| 2003/0104030 | A1 | 6/2003 | Igaki et al. |
| 2004/0200729 | A1 | 10/2004 | Boulais et al. |
| 2005/0010282 | A1 | 1/2005 | Thornton et al. |
| 2005/0038504 | A1 | 2/2005 | Halleriet et al. |
| 2005/0074544 | A1 | 4/2005 | Pacetti et al. |
| 2005/0079274 | A1 | 4/2005 | Palasis et al. |
| 2007/0259102 | A1 | 11/2007 | McNiven et al. |
| 2008/0152944 | A1 | 6/2008 | Bonini et al. |
| 2008/0208310 | A1 | 8/2008 | McDermott et al. |
| 2008/0233267 | A1 | 9/2008 | Berglund |
| 2009/0035351 | A1 | 2/2009 | Berglund et al. |
| 2009/0143855 | A1 | 6/2009 | Weber et al. |
| 2010/0018602 | A1 | 1/2010 | Chappa |
| 2010/0068404 | A1 | 3/2010 | Wang et al. |
| 2011/0008405 | A1 | 1/2011 | Birdsall et al. |
| 2011/0034992 | A1 | 2/2011 | Papp |
| 2011/0070357 | A1 | 3/2011 | Mitchell et al. |
| 2011/0264187 | A1 | 10/2011 | Melder |
| 2012/0067008 | A1 | 3/2012 | Bienvenu |
| 2012/0067454 | A1 | 3/2012 | Melder |
| 2012/0070562 | A1 | 3/2012 | Avelar et al. |
| 2012/0216907 | A1 | 8/2012 | Pacetti |
| 2014/0163664 | A1 | 6/2014 | Goldsmith |
| 2014/0295093 | A1 | 10/2014 | Hirao |

OTHER PUBLICATIONS

U.S. Appl. No. 61/244,050, filed Sep. 20, 2009, Silver et al.
Kim et al. "Electrically Controlled Hydrophobicity in a Surface Modified Nanoporous Carbon" Applied Physics Letters 98, 053106 (2011).
Vallet et al. "Electrowetting of Water and Aqueous Solutions on Poly(ethylene Terephthalate) Insulating Films" Polymer vol. 37, No. 12, pp. 2465-2470, 1996.
JP 2015-508939, 1st Japanese Office Action, dated Nov. 25, 2016.

APPARATUS AND METHODS FOR FILLING A DRUG ELUTING MEDICAL DEVICE VIA CAPILLARY ACTION

FIELD OF THE INVENTION

The invention relates generally to implantable medical devices that release a therapeutic substance or drug, and more particularly to apparatuses and methods of loading or filling such medical devices with the therapeutic substance or drug.

BACKGROUND OF THE INVENTION

Drug-eluting implantable medical devices are useful for their ability to provide structural support while medically treating the area in which they are implanted. For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include sirolimus and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a drug or a combination of drugs. Once the medical device is implanted at a target location, the drug is released from the polymer for treatment of the local tissues. The drug is released by a process of diffusion through a polymer layer of a biostable polymer, and/or as the polymer material degrades when the polymer layer is of a biodegradable polymer.

Drug impregnated polymer coatings are limited in the quantity of the drug to be delivered by the amount of a drug that the polymer coating can carry and the size of the medical device. As well, controlling the rate of elution using polymer coatings is difficult.

Accordingly, drug-eluting medical devices that enable increased quantities of a drug to be delivered by the medical device, and allow for improved control of the elution rate of the drug, and improved methods of forming such medical devices are needed. Co-pending U.S. Patent Application Publication No. 2011/0008405, filed Jul. 9, 2009, U.S. Provisional Application No. 61/244,049, filed Sep. 20, 2009, U.S. Provisional Application No. 61/244,050, filed Sep. 20, 2009, and co-pending U.S. Patent Application Publication No. 2012/0067008, each incorporated by reference herein in their entirety, disclose methods for forming drug-eluting stents with hollow wires. Drug-eluting stents formed with hollow wires can achieve similar elution curves as drug-eluting stents with the therapeutic substance disposed in a polymer on the surface of the stent. Drug-eluting stents formed with hollow wires achieving similar elution curves as drug-polymer coated stent are expected to have similar clinical efficacy while simultaneously being safer without the polymer coating. In addition, a variety of elution curves can be achieved from drug-eluting stents formed with hollow wires. In some applications, such as coronary stents, the diameter of the hollow wire lumen to be filled with the drug or therapeutic substance is extremely small, e.g. about 0.0015 in., which may make filling the lumen difficult. As such, improved apparatus for and methods of filling or loading a therapeutic substance or drug within a lumen of a hollow wire of a stent are needed.

BRIEF SUMMARY OF THE INVENTION

Embodiments hereof are directed to methods and apparatus for filling a fluid drug formulation within a lumenal space of a hollow wire that forms a stent. A filling chamber of an apparatus is caused to reach a vapor-liquid equilibrium of a solvent of the fluid drug formulation. The filling chamber houses a reservoir containing a wicking means and the apparatus includes a valve positioned between the filling chamber and a loading chamber and the valve is closed such that the filling chamber and loading chamber are not in fluid communication. A liquid is added into a container housed within the filling chamber after the filling chamber has reached the vapor-liquid equilibrium of a solvent of the fluid drug formulation. The fluid drug formulation is added into the reservoir containing the wicking means after the filling chamber has reached the vapor-liquid equilibrium of a solvent of the fluid drug formulation. The fluid drug formation and the wicking means is mixed within the reservoir. A stent formed from a hollow wire is placed within the loading chamber of the apparatus. The loading chamber of the apparatus is caused to reach the vapor-liquid equilibrium of the solvent of the fluid drug formulation. After both the filling chamber and the loading chamber have reached the vapor-liquid equilibrium of a solvent of the fluid drug formulation, the valve is opened such that the filling chamber and loading chamber are in fluid communication. The stent is moved from the loading chamber of the apparatus into the filling chamber of the apparatus while the valve is opened, and the valve is closed such that the filling chamber and loading chamber are not in fluid communication after the stent is housed in the filling chamber. At least a portion of the stent is placed into contact with the wicking means within the filling chamber such that the lumenal space of the hollow wire that forms the stent is in fluid contact with the wicking means. Contact is maintained between the wicking means and the stent until a lumenal space defined by the hollow wire is at least partially filled with the fluid drug formulation via capillary action.

In another embodiment hereof, a filling chamber of an apparatus is caused to reach a vapor-liquid equilibrium of a solvent of a fluid drug formulation. The filling chamber houses a reservoir containing a wicking means and the apparatus includes a valve positioned between the filling chamber and a loading chamber and the valve is closed such that the filling chamber and loading chamber are not in fluid communication. The fluid drug formulation is added into the reservoir containing the wicking means after the filling chamber has reached the vapor-liquid equilibrium of a solvent of the fluid drug formulation. An implantable medical device formed from a hollow wire is placed within the loading chamber of the apparatus. The implantable medical device is transferred from the loading chamber into the filling chamber by opening the valve such that the filling chamber and loading chamber are in fluid communication, moving the implantable medical device into the filling chamber while the valve is open, and closing the valve such that the filling chamber and loading chamber are no longer in fluid communication after the implantable medical device is housed within the filling chamber. At least a portion of the implantable medical device is placed into contact with the wicking means within the filling chamber such that the lumenal space of the hollow wire that forms the implantable medical device is in fluid contact with the wicking means.

Contact is maintained between the wicking means and the implantable medical device until at least the lumenal space defined by the hollow wire is at least partially filled with the fluid drug formulation via capillary action.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well, poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Drug eluting stents described herein may be utilized in the context of treatment of blood vessels such as the coronary, carotid and renal arteries, or any other body passageways where it is deemed useful. More particularly, drug eluting stents loaded with a therapeutic substance by methods described herein are adapted for deployment at various treatment sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents. Furthermore, there is no intention to be bound by any expressed or implied theory presented in the preceding technical field, background, brief summary or the following detailed description.

Hollow Wire Drug-Eluting Stent

Figure 1:
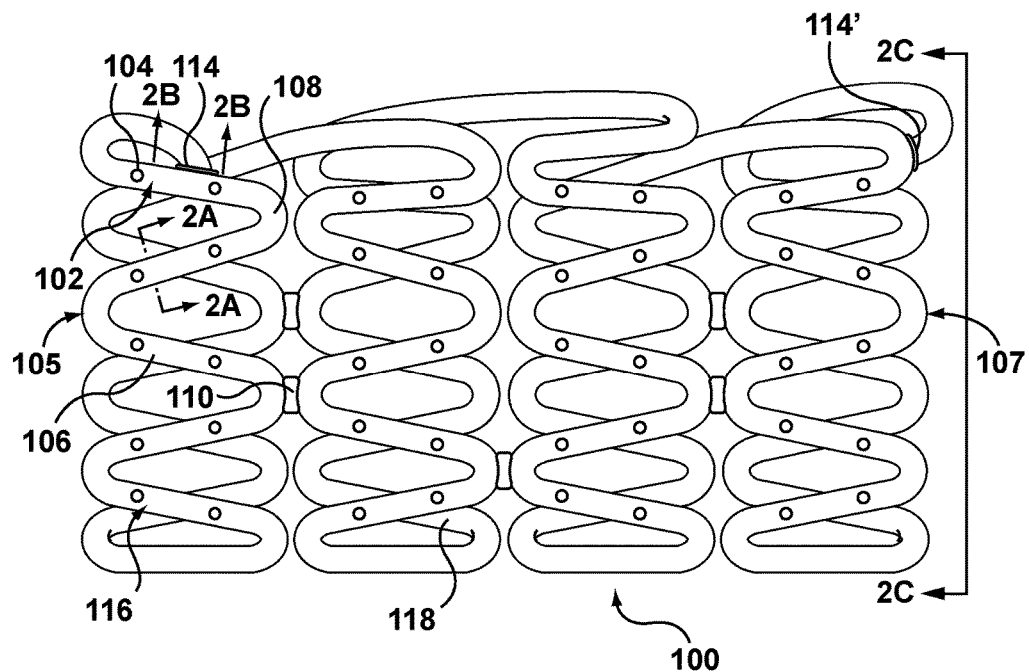
FIG. 1 is a side view of a drug eluting stent formed from a hollow wire according to one embodiment hereof.
Figures 2A, 2B, 2C:
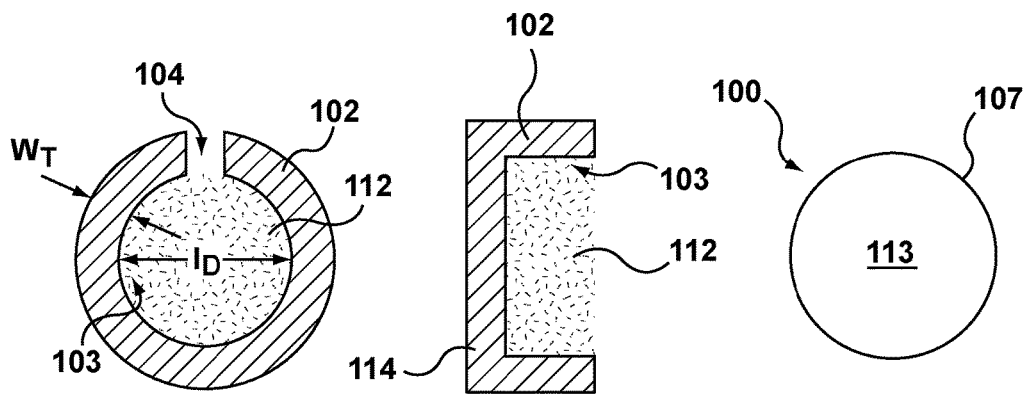
FIG. 2A is a cross-sectional view taken along line 2A-2A of FIG. 1.
FIG. 2B is a sectional view taken along line 2B-2B at an end of the hollow wire of FIG. 1.
FIG. 2C is an end view taken along line 2C-2C of FIG. 1

An embodiment of a stent 100 to be loaded with a drug in accordance with embodiments hereof is shown in FIGS. 1-2C. Stent 100 is formed from a hollow strut or wire 102 and hereinafter may be referred to as a stent or a hollow core stent. Hollow wire 102 defines a lumen or lumenal space 103, which may be formed before or after being shaped into a desired stent pattern. In other words, as used herein, "a stent formed from a hollow wire" includes a straight hollow wire shaped into a desired stent pattern or a stent constructed from any suitable manufacturing method that results in a tubular component formed into a desired stent pattern, the tubular component having a lumen or lumenal space extending continuously there through. As shown in FIG. 1, hollow wire 102 is formed into a series of generally sinusoidal waves including generally straight segments 106 joined by bent segments or crowns 108 to form a waveform that is wound around a mandrel or other forming device to form a generally cylindrical stent 100 that defines a central blood flow passageway or lumen 113 (shown in FIG. 2C) there through that extends from a first end or tip 105 to a second end or tip 107 of stent 100. Selected crowns 108 of longitudinally adjacent turns of the waveform may be joined by, for example, fusion points or welds 110 as shown in FIG. 1. Methods of filling a drug within a stent in accordance with embodiments hereof are not limited to stents having the pattern shown in FIG. 1. Stents formed into any pattern suitable for use as a stent may be loaded with a drug by the methods disclosed herein. For example, and not by way of limitation, stents formed into patterns disclosed in U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety, may be loaded with a drug by the methods disclosed herein.

As shown in FIG. 2A, hollow wire 102 of stent 100 allows for a therapeutic substance or drug 112 to be deposited within lumen or lumenal space 103 of hollow wire 102. Although lumen 103 is shown as uniformly filled with therapeutic substance or drug 112 in FIG. 2A, therapeutic substance or drug 112 is not required to fill or be uniformly dispersed within the lumenal space 103 of hollow wire 102 but is only required to occupy at least a portion of the lumenal space. Stated another way, in an embodiment hereof, luminal space 103 may be intentionally or purposely only partially filled. Lumen 103 may continuously extend from a first end 114 to a second end 114' of hollow wire 102. Although hollow wire 102 is shown as generally having a circular cross-section, hollow wire 102 may be generally elliptical or rectangular in cross-section. Hollow wire 102 may have a wall thickness $W_T$ in the range of 0.0004 to 0.005 inch with an inner or lumen diameter $I_D$ ranging from 0.0005 to 0.02 inch. Hollow wire 102 that forms stent 100 may be made from a metallic material for providing artificial radial support to the wall tissue, including but not limited to stainless steel, nickel-titanium (nitinol), nickel-cobalt alloy such as MP35N, cobalt-chromium, tantalum, titanium, platinum, gold, silver, palladium, iridium, and the like. Alternatively, hollow wire 102 may be made from a hypotube, which is a hollow metal tube of a very small diameter of the type typically used in manufacturing hypodermic needles. Alternatively, hollow wire 102 may be formed from a non-metallic material, such as a polymeric material. The polymeric material may be biodegradable or bioresorbable such that stent 100 is absorbed in the body after being utilized to restore patency to the lumen and/or provide drug delivery.

Hollow wire 102 further includes drug-delivery side openings or ports 104 dispersed along its length to permit therapeutic substance or drug 112 to be released from lumen 103. Side openings 104 may be disposed only on generally straight segments 106 of stent 100, only on crowns 108 of stent 100, or on both generally straight segments 106 and crowns 108. Side openings 104 may be sized and shaped as desired to control the elution rate of drug 112 from stent 100. More particularly, side openings 104 may be slits or may be holes having any suitable cross-section including but not limited to circular, oval, rectangular, or any polygonal cross-section. Larger sized side openings 104 generally permit a faster elution rate and smaller sized side openings 104 generally provide a slower elution rate. Further, the size and/or quantity of side openings 104 may be varied along stent 100 in order to vary the quantity and/or rate of drug 112 being eluted from stent 100 at different portions of stent 100. Side openings 104 may be, for example and not by way of limitation, 5-30 µm in width or diameter. Side openings 104 may be provided only on an outwardly facing or ablumenal surface 116 of stent 100, as shown in FIG. 2, only on the inwardly facing or lumenal surface 118 of stent 100, on both surfaces, or may be provided anywhere along the circumference of wire 102.

In various embodiments hereof, a wide range of therapeutic agents or drugs may be utilized as the elutable therapeutic substance or drug 112 contained in lumen 103 of hollow wire 102, with the pharmaceutically effective amount being readily determined by one of ordinary skill in the art and ultimately depending, for example, upon the condition to be treated, the nature of the therapeutic agent itself, the tissue into which the dosage form is introduced, and so forth. Further, it will be understood by one of ordinary skill in the art that one or more therapeutic substances or drugs may be loaded into hollow wire 102. Therapeutic substance or drug 112 delivered to the area of a stenotic lesion can be of the type that dissolves plaque material forming the stenosis or can be an anti-platelet formation drug, an anti-thrombotic drug, or an anti-proliferative drug. Such drugs can include TPA, heparin, urokinase, sirolimus or analogues of sirolimus, for example. Of course stent 100 can be used for delivering any suitable medications to the walls and interior of a body vessel including one or more of the following: anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In accordance with embodiments hereof, stent 100 is loaded or filled with therapeutic substance or drug 112 prior to implantation into the body. Therapeutic substance or drug 112 is generally mixed with a solvent or dispersion medium/dispersant in order to be loaded into lumen 103 of hollow wire 102. In addition, the therapeutic substance or drug 112 can be mixed with an excipient to assist with elution in addition to the solvent or dispersion medium/dispersant in order to be loaded into lumen 103 of hollow wire 102. Hereinafter, the term "fluid drug formulation" may be used to refer generally to therapeutic substance or drug 112, a solvent or dispersion medium, and any excipients/additives/modifiers added thereto. In one embodiment, therapeutic substance or drug 112 is mixed with a solvent or solvent mixture as a solution before being loaded into hollow wire 102. A solution is a homogeneous mixture in which therapeutic substance or drug 112 dissolves within a solvent or a solvent mixture. In one embodiment, a solution includes a high-capacity solvent which is an organic solvent that has a high capacity to dissolve therapeutic substance or drug 112. High capacity as utilized herein is defined as an ability to dissolve therapeutic substance or drug 112 at concentrations greater than 500 mg of substance per milliliter of solvent. Examples of high capacity drug dissolving solvents for sirolimus and similar substances include but are not limited to tetrahydrofuran (THF), di-chloromethane (DCM), chloroform, and di-methyl-sulfoxide (DMSO). In addition to the high-capacity solvent, a solution may include an excipient to assist in drug elution. In one embodiment, an excipient may be a surfactant such as but not limited to sorbitan fatty acid esters such as sorbitan monooleate and sorbitan monolaurate, polysorbates such as polysorbate 20, polysorbate 60, and polysorbate 80, cyclodextrins such as 2-hydroxypropyl-beta-cyclodextrin and 2,6-di-O-methyl-beta-cyclodextrin, sodium dodecyl sulfate, octyl glucoside, and low molecular weight poly(ethylene glycol)s. In another embodiment, an excipient may be a hydrophilic agent such as but not limited to salts such as sodium chloride and other materials such as urea, citric acid, and ascorbic acid. In yet another embodiment, an excipient may be a stabilizer such as but not limited to butylated hydroxytoluene (BHT). Depending on the desired drug load, a low capacity solvent can also be chosen for its reduced solubility of therapeutic substance or drug 112. Low capacity is defined as an ability to dissolve therapeutic substance or drug 112 at concentrations typically below 500 mg of drug per milliliter solvent. Examples of low capacity drug dissolving solvents for sirolimus and similar substances include but are not limited to methanol, ethanol, propanol, acetonitrile, ethyl lactate, acetone, and solvent mixtures like tetrahydrofuran/water (9:1 weight ratio). After a solution is loaded into stent 100, therapeutic substance or drug 112 may be precipitated out of the solution, e.g., transformed into solid phase, and the majority of the residual solvent and any nonsolvent, if present, may be extracted from the lumenal space of hollow wire 102 such that primarily only therapeutic substance or drug 112 or therapeutic substance or drug 112 and one or more excipients remain to be eluted into the body.

In another embodiment, therapeutic substance or drug 112 is mixed with a dispersion medium as a slurry/suspension before being loaded into hollow wire 102. In a slurry/suspension form, therapeutic substance or drug 112 is not dissolved but rather dispersed as solid particulate in a dispersion medium, which refers to a continuous medium in liquid form within which the solid particles are dispersed. Examples of dispersion mediums with an inability to dissolve therapeutic substance or drug 112 depend on the properties of therapeutic substance or drug 112. For example, suitable dispersion mediums with an inability to dissolve sirolimus include but are not limited to water, hexane, and other simple alkanes, e.g., C5 thru C10. Certain excipients, suspending agents, surfactants, and/or other additives/modifiers can be added to the drug slurry/suspension to aid in suspension and stabilization, ensure an even dispersion of drug throughout the suspension and/or increase the surface lubricity of the drug particles. Surfactants thus generally prevent therapeutic substance or drug 112 from floating on the top of or sinking to the bottom of the dispersion medium and also prevent particles of therapeutic substance of drug 112 from clumping. Examples of surfactants include but are not limited to sorbitan fatty acid esters such as sorbitan monooleate and sorbitan monolaurate, polysorbates such as polysorbate 20, polysorbate 60, and polysorbate 80, and cyclodextrins such as 2-hydroxypropyl-beta-cyclodextrin and 2,6-di-O-methyl-beta-cyclodextrin. In one embodiment, the targeted amount of therapeutic substance or drug 112 is suspended in the dispersion medium and the appropriate additive/modifier is added on a 0.001 to 10 wt % basis of total formulation. In addition, an excipient such as urea or 2,6-di-O-methyl-beta-cylcodextrin may be added to the slurry/suspension to assist in drug elution.

Open ends 114, 114' of wire 102 may be closed or sealed either before or after the drug is loaded within lumen 103 as shown in the sectional view of FIG. 2B, which is taken along line 2B-2B of FIG. 1. Once positioned inside of the body at the desired location, stent 100 is deployed for permanent or temporary implantation in the body lumen such that therapeutic substance or drug 112 may elute from lumen 103 via side openings 104.

Filling Process Via Capillary Action

Embodiments hereof relate to the use of capillary action to fill lumen 103 of hollow wire 102. Capillary action as used herein relates to the ability of a liquid to flow in narrow spaces without the assistance of, and in opposition to, external forces like gravity. As will be explained in further detail herein, only a portion of stent 100 having an opening (i.e., at least one side hole 104, first end 114 of hollow wire 102, or second or opposing end 114' of hollow wire 102) is required to be submerged or exposed to a fluid drug formulation, or submerged or exposed to a wicking means in contact with a fluid drug formulation such that the lumenal space of hollow wire 102 that forms stent 100 is in fluid contact with the wicking means. The fluid drug formulation will then wick or travel into lumen 103 of hollow wire 102 via submerged/exposed holes 104 (or first end 114 of hollow wire 102, or second or opposing end 114' of hollow wire 102) and fill or load the entire length of lumen 103 via capillary action. Capillary action occurs because of intermolecular attractive forces between the fluid drug formulation and hollow wire 102. When lumen 103 of hollow wire 102 is sufficiently small, then the combination of surface tension and adhesive forces formed between the fluid drug formulation and hollow wire 102 act to lift the fluid drug formulation and fill the hollow wire. Filling stents 100 via capillary action result in a filling method that streamlines the drug filling process because such a method may be utilized to batch fill a plurality of stents in a relatively short time period. In addition, filling stents 100 via capillary action reduces drug load variability and makes the drug fill process more controllable and predictable. Capillary action results in fluid drug formulation uniformly filling or deposited within lumen 103 of hollow wire 102, and after solvent/dispersion medium extraction which is described in more detail below, lumen 103 of hollow wire 102 has a uniform drug content along its length.

Figure 3:
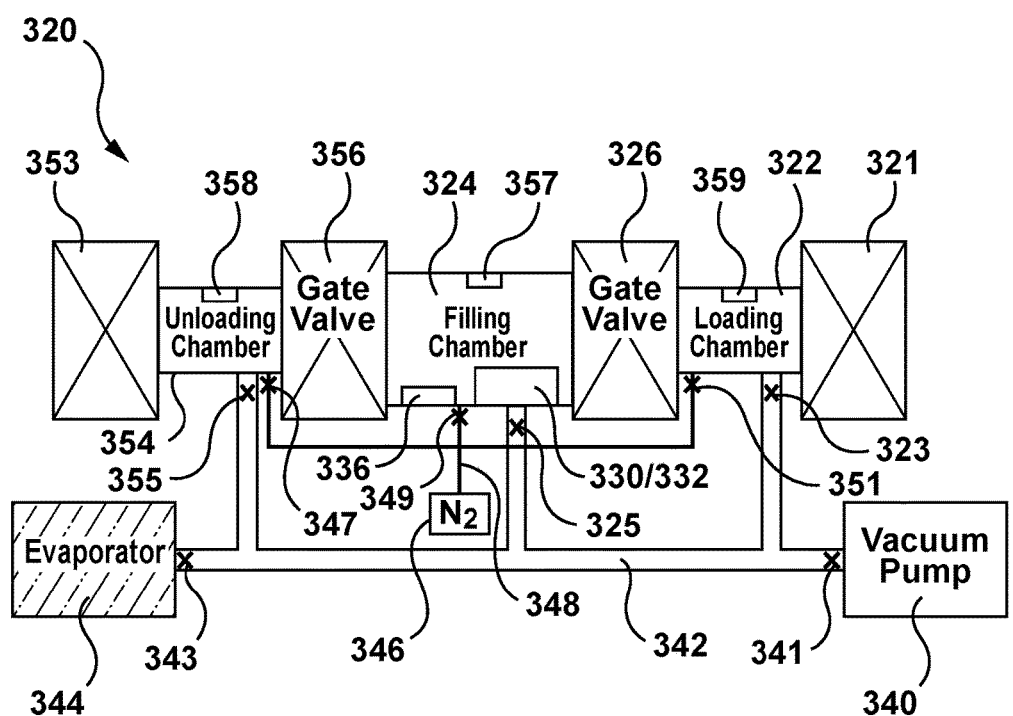
FIG. 3 is a schematic illustration of an apparatus for filling a plurality of stents of FIG. 1 with a fluid drug formulation via capillary action.
Figure 4:
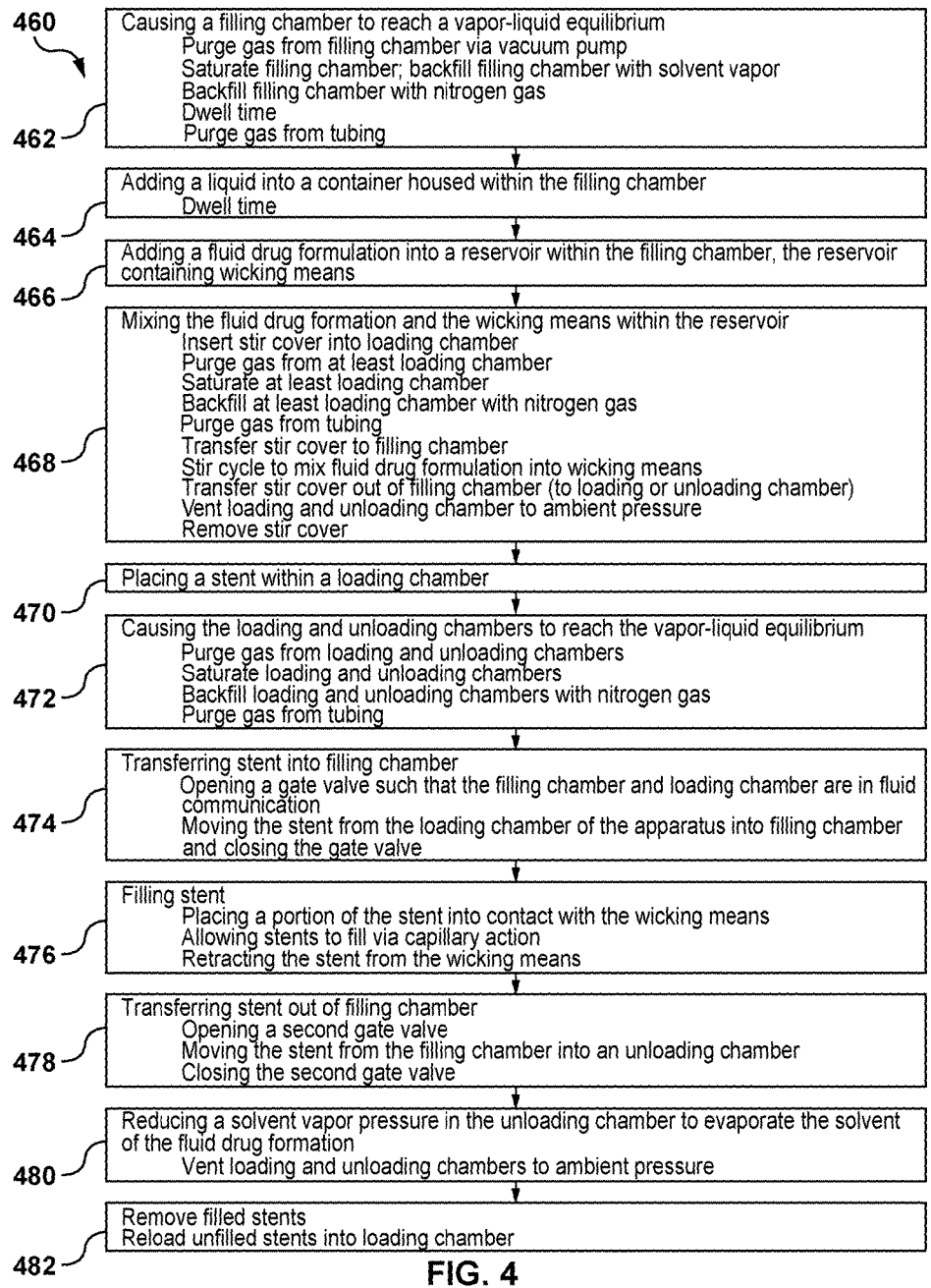
FIG. 4 is a flow chart of a method for filling a plurality of stents of FIG. 1 with a fluid drug formulation via capillary action.

More particularly, FIG. 3 is a schematic illustration of an apparatus 320 which may be utilized to perform the method steps illustrated in the flow chart of FIG. 4, which describes a method 460 for filling lumen 103 of a stent 100 with a fluid drug formulation 334 via capillary action. FIG. 4 will be described in conjunction with FIGS. 5-24. As will be described in more detail herein, FIGS. 5-24 represent an embodiment hereof in which apparatus 320 includes multiple valves and separate air-tight or air-locked chambers to efficiently mass produce a batch of drug-filled stents 100 via capillary action. "Chamber" has used herein does not have a size constraint but rather includes any enclosed space regardless of the size thereof which may vary according to application. The valves or airlocks are cycled between ambient conditions to a condition which suppresses formulation evaporation and allows for more drug-filled stent parts per formulation volume. Apparatus 320 and method 460 may be used to fill tens of thousands of stents 100 at a time via the multiple air-locked chambers and quicker saturation process thereof. For illustrative purposes only, stents 100 are represented as straight tubular structures in FIGS. 5-24 although it will be understood by one of ordinary skill in the art that stents 100 are a hollow wire shaped into a desired stent pattern as previously described with reference to FIG. 1.

With reference to FIG. 3, apparatus 320 includes a first or filling chamber 324, a second or loading chamber 322, and a third or unloading chamber 354. Filling chamber 324 is separated from loading chamber 322 via a first gate valve 326 positioned there-between, and similarly filling chamber 324 is separated from unloading chamber 354 via a second gate valve 356 positioned there-between. Each valve gate 326, 356 is operable to alternate between an open configuration in which the adjacent chambers are in fluid communication, and a closed configuration in which the adjacent chambers are not in fluid communication. More particularly, when first gate valve 326 is closed, filling chamber 324 is not in fluid communication with loading chamber 322 and filling chamber 324 is air-tight, air-locked, or otherwise sealed with respect to loading chamber 322. When first gate valve 326 is open, filling chamber 324 is in fluid communication with loading chamber 322. Similarly, when second gate valve 356 is closed, filling chamber 324 is not in fluid communication with unloading chamber 354 and filling chamber 324 is air-tight, air-locked, or otherwise sealed with respect to unloading chamber 354. When second gate valve 356 is open, filling chamber 324 is in fluid communication with unloading chamber 354. Thus, if first gate valve 326 and second gate valve 356 are both simultaneously open, filling chamber 324, loading chamber 322, and unloading chamber 354 are in fluid communication with each other. Loading and unloading chambers 322, 354 each include a vent 359, 358, respectively, and filling chamber 324 includes a vent 357 to be utilized in the method of filling stents 100 as described in more detail herein.

In addition to valve gates 326, 356, apparatus 320 includes a valve or sealable door 321 adjacent to loading chamber 322 and a valve or sealable door 353 adjacent to unloading chamber 354. Sealable doors 321, 353 permit stents 100 and other components utilized in the method of filling stents 100 to be loaded and unloaded from loading and unloading chambers 322, 354, respectively.

Filling chamber 324 includes a first reservoir 332 which houses or holds wicking means 330 and a fluid drug formulation 334 that includes therapeutic substance or drug 112. In FIG. 3 (as well as FIGS. 5-8), reservoir 332 is shown empty but is denoted as 330/332 to indicate the presence of wicking means 330 therein. Wicking means 330 according to an embodiment hereof is shown in more detail in FIGS. 20 and 21, and is described in more detail herein. Reservoir 332 is shown being filled with fluid drug formation 334 in FIG. 9 during description of the method of use. In all figures, when present, fluid drug formation 334 is illustrated within reservoir 332 via the same cross-hatch pattern as shown in FIG. 9. Wicking means 330 is in contact with fluid drug formulation 334 to control transfer of the fluid drug formulation 334 into lumen 103 of hollow wire 102 during the capillary filling procedure as described in FIGS. 5-24. "Wicking means" as used herein refers to a medium or component that acts or functions to move or convey, or acts or functions to assist in the movement of, the fluid drug formulation 334 by capillary action from within reservoir 332 into lumen 103 of hollow wire 102. In addition to controlling transfer of the fluid drug formulation, in some embodiments hereof, wicking means 330 also removes excess fluid drug formulation from the exterior surfaces of hollow wire 102 of stent 100 when stent 100 is retracted out of the wicking means. When wicking means 330 performs this excess removal function, an additional processing or cleaning step may not be required to make stents 100 free or substantially free of drug residue on the exterior surfaces of hollow wire 102. Wicking means 330 preferably has several characteristics or properties, including that it does not degrade or add contaminants into fluid drug formulation 334, that it does not change mechanical, dimensional, and or electrical properties, that it is inert in fluid drug formulation 334, that it does not cause a phase separation within fluid drug formulation 334, that is does not change the formulation in any measurable way, and that it is usable and/or stable for several days or weeks meaning that it does not change in any measurable way. As will be described in more detail with respect to FIGS. 21 and 22, wicking means 330 is a plurality of ceramic beads with fluid drug formulation 334 evenly dispersed within.

Filling chamber 324 also includes an open reservoir or container 336 which is filled with a liquid 338. Container 336 is shown empty in FIG. 3, but is shown being filled with liquid 338 in FIG. 8 during description of the method of use. In all figures, when present, liquid 338 is illustrated within container 336 via the same cross-hatch pattern as FIG. 8. Container 336 is any structure suitable for housing or containing a relatively large volume of liquid with high surface area which serves as a solvent vapor source as will be described in more detail herein. Liquid 338 is utilized in the method of filling stents 100 to prevent evaporation of solvent from fluid drug formation 334 contained within reservoir 332 as described in more detail herein. Further, filling chamber 324, loading chamber 322, and unloading chamber 354 are selectively in fluid communication with a supply of nitrogen gas 346 via tubing network 348. Tubing network 348 includes valves 351, 349, 347 which may be opened to allow filling chamber 324, loading chamber 322, unloading chamber 354, respectively, to be in fluid communication with the supply of nitrogen gas 346 and which may be closed to cause filling chamber 324, loading chamber 322, unloading chamber 354, respectively, to no longer be in fluid communication with the supply of nitrogen gas 346. Nitrogen gas 346 may be utilized in the method of filling stents 100 as described in more detail herein.

Apparatus 320 further includes a vacuum pump 340 and an evaporator 344 which are each selectively in fluid communication with loading chamber 322, filling chamber 324, and unloading chamber 354 via a tubing network 342. Valve 341 adjacent to vacuum pump 340 may be opened to allow tubing network 342 to be in fluid communication with vacuum pump 340 and may be closed to cause tubing network 342 to no longer be in fluid communication with vacuum pump 340. Valve 343 adjacent to evaporator 344 may be opened to allow tubing network 342 to be in fluid communication with evaporator 344 and may be closed to cause tubing network 342 to no longer be in fluid communication with evaporator 344. Evaporator 344 is a separate chamber containing a supply of liquid and vapor solvent that is the same as or similar to the solvent utilized in fluid drug formation 334. As described above, examples of low capacity drug dissolving solvents include but are not limited to methanol, ethanol, propanol, acetonitrile, ethyl lactate, acetone, and solvent mixtures like tetrahydrofuran/water (9:1 weight ratio).

Tubing network 342 includes a valve 323 for selectively controlling fluid communication with loading chamber 322, a valve 325 for selectively controlling fluid communication with filling chamber 324, and a valve 355 for selectively controlling fluid communication with unloading chamber 354. More particularly, when valve 323 is closed, loading chamber 322 is not in fluid communication with tubing network 342 and loading chamber 322 is air-tight, air-locked, or otherwise sealed with respect to tubing network 342. When valve 323 is open, loading chamber 322 is in fluid communication with tubing network 342. Similarly, when valve 325 is closed, filling chamber 324 is not in fluid communication with tubing network 342 and filling chamber 324 is air-tight, air-locked, or otherwise sealed with respect to tubing network 342. When valve 325 is open, filling chamber 324 is in fluid communication with tubing network 342. Similarly, when valve 355 is closed, unloading chamber 354 is not in fluid communication with tubing network 342 and unloading chamber 354 is air-tight, air-locked, or otherwise sealed with respect to tubing network 342. When valve 355 is open, unloading chamber 354 is in fluid communication with tubing network 342. Valve 343 adjacent to evaporator 344 in conjunction with valves 323, 325, 355 control which chamber will be filled with vapor that supplied from evaporator 344 and valve 341 adjacent to vacuum pump 340 in conjunction with valves 323, 325, 355 control which chamber will have residual gas purged therefrom via vacuum pump 340.

FIGS. 5-24 illustrate the various steps of method 460. In FIGS. 5-24, the cross-hatch pattern of various components is utilized to indicate the contents of thereof. More particularly, the cross-hatch pattern shown in FIG. 5 of loading and unloading chambers 322, 354 indicates residual vapor, gas, or other mixed components may be present therein. When any chambers and/or tubing network 342 are empty (such as filling chamber 324 in FIG. 5), the emptiness indicates that any residual vapor, gas, or other mixed components have been purged therefrom. When any chambers and/or tubing network 342 are filled with a vapor 345, the cross-hatch pattern shown in FIG. 6 of filling chamber 324 and tubing network 342 indicates that vapor 345 is present therein. Further, as previously described, when fluid drug formation 334 is present within reservoir 332, its presence is indicated via the cross-hatch pattern utilized in FIG. 9. In addition, as previously described, when liquid 338 is present within container 336, its presence is indicated via the cross-hatch pattern utilized in FIG. 8.

Figure 5:
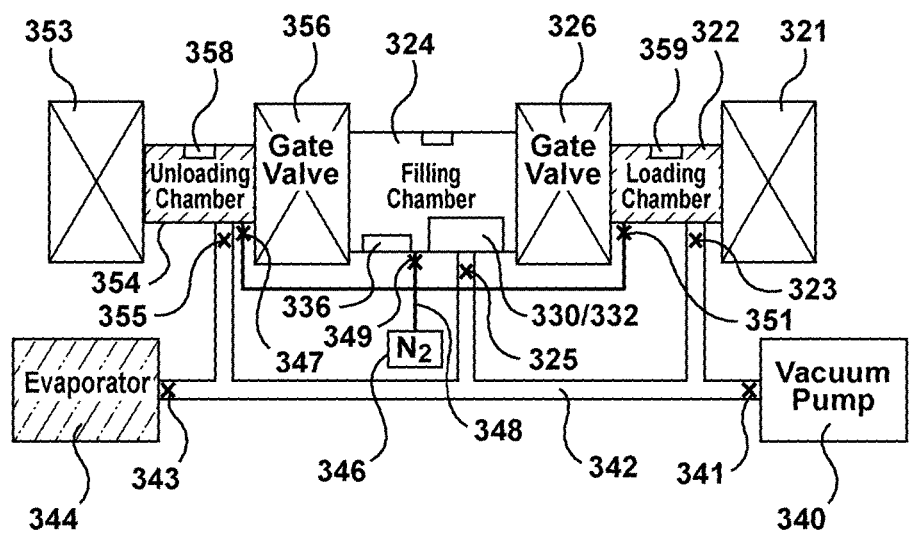
FIG. 5 is a schematic illustration of the apparatus of FIG. 3 being utilized to perform the first step of the flow chart of FIG. 4, wherein gas is purged from a filling chamber of the apparatus via a vacuum pump.
Figure 6:
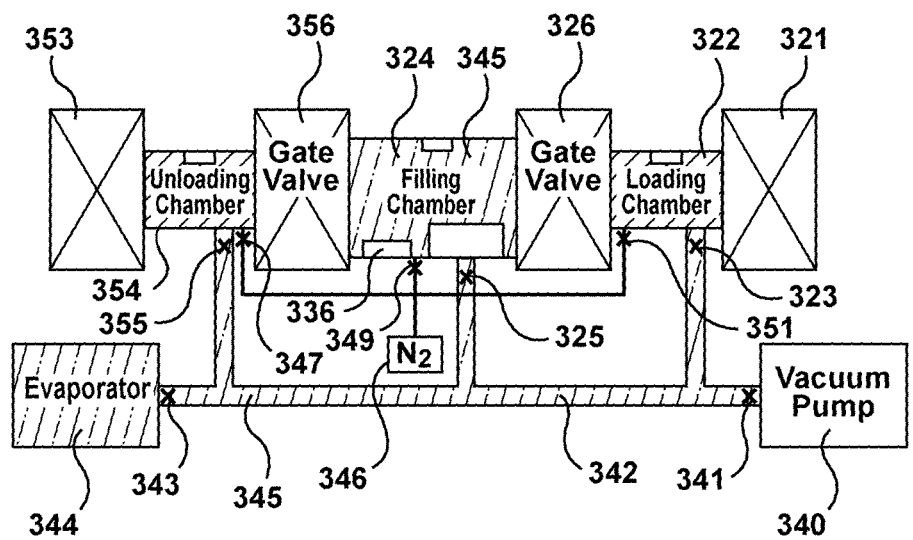
FIG. 6 is a schematic illustration of the apparatus of FIG. 3 being utilized to perform the first step of the flow chart of FIG. 4, wherein the filling chamber is saturated with solvent vapor.
Figure 7:
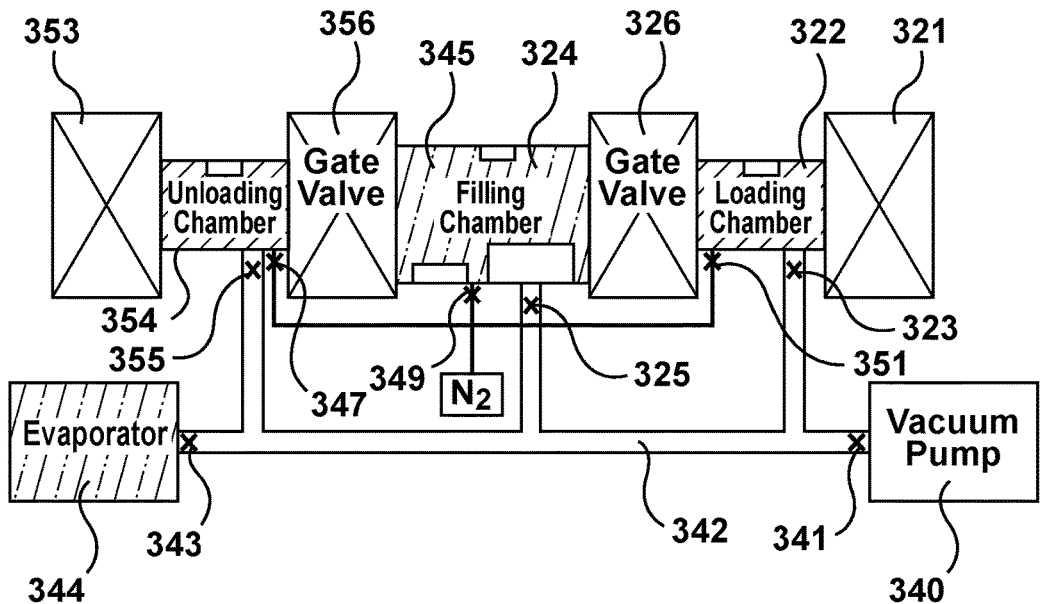
FIG. 7 is a schematic illustration of the apparatus of FIG. 3 being utilized to perform the first step of the flow chart of FIG. 4, wherein gas is purged from network tubing of the apparatus via the vacuum pump.

Turning now to FIGS. 5-7, a first step 462 of method 460 illustrated in FIG. 4 will be described. First step 462 includes causing filling chamber 324 to reach a vapor-liquid equilibrium of a solvent of fluid drug formulation 334. Prior to the initiation of first step 462, both first and second valve gates 326, 356 are closed such that filling chamber 324, loading chamber 322, and unloading chamber 354 are distinct or separate closed chambers and are not in fluid communication with each other. Valve 325 is open such that filling chamber 324 is in fluid communication with tubing network 342, but valves 323, 355 are closed such that loading and unloading chambers 322, 354, respectively, are not in fluid communication with tubing network 342. Valve 343 adjacent to evaporator 344 is closed. Prior to performing first step 462 of method 460, a preparation cycle may be performed multiple times within filling chamber 324. The preparation cycle includes removing the gas within filling chamber 324 and tubing network 342 by opening valve 341 to vacuum pump 340 and then backfilling filling chamber 324 with nitrogen gas 346 by opening valve 349 until filling chamber 324 reaches atmospheric pressure or another predetermined or set pressure.

Once the preparation cycle is repeated as desired, first step 462 of method 460 is performed and the gas within filling chamber 324 and tubing network 342 is purged by opening valve 341 to vacuum pump 340 as shown in FIG. 5. Vacuum pump 340 lowers the pressure within filling chamber 324 to a pressure lower than atmospheric pressure. Via vacuum pump 340, any residual vapor, gas, or other mixed components are purged from filling chamber 324 and the pressure in filling chamber 324 and tubing network 342 may be between 0 PSIA and 14.7 PSIA (0 Torr and 760 Torr).

With reference to FIG. 6, after gas is purged from filling chamber 324 and tubing network 342 via vacuum pump 340, valve 341 is closed and then valve 343 is opened to backfill tubing network 342 and filling chamber 324 with a vapor 345 of the solvent of fluid drug formation 334 via evaporator 344 which houses a supply of the vapor. Filling chamber 324 is saturated with a vapor of the solvent of fluid drug formation 334 via evaporator 344 such that filling chamber 324 reaches solvent vapor saturation. Stated another way, filling chamber 324 is at the vapor-liquid equilibrium of the solvent of fluid drug formulation 334. When vapor-liquid equilibrium is reached, valve 343 and valve 325 are closed. Vapor-liquid equilibrium is the condition or state where a liquid and its vapor are in equilibrium with each other, where the rate of evaporation equals the rate of condensation such that there is no net or mass transport across its respective phase. Such an equilibrium is practically reached in a closed location if a liquid and its vapor are allowed to stand in contact with each other for a sufficient time period. As used herein, the term "the vapor-liquid equilibrium" or "solvent vapor saturation" includes absolute pressures of ±5 torr within theoretical values that are stated by vapor pressure curves generated via Antoine Coefficients for a particular solvent at a particular temperature. As described above, examples of low capacity drug dissolving solvents include but are not limited to methanol, ethanol, propanol, acetonitrile, ethyl lactate, acetone, and solvent mixtures like tetrahydrofuran/water (9:1 weight ratio). Evaporation is considered very slow and practically negligible within this range of absolute pressure, and the filling process may be performed within this range of pressure without premature precipitation of therapeutic substance or drug 112 within lumen 103 of hollow wire 102. Valves 343, 325 are then closed.

In an embodiment, after backfilling tubing network 342 and filling chamber 324 with vapor 345 of the solvent of fluid drug formation 334 via evaporator 344, filling chamber 324 may be backfilled with nitrogen gas 346 by opening valve 349 for stabilization of filling chamber 324. Adding nitrogen gas 346 to filling chamber 324 enhances stability and prevents temperature fluctuations within the chamber and system when the filling chamber is saturated with a vapor of the solvent of fluid drug formulation 334 as described above with respect to FIG. 6. Absolute pressure in filling chamber 324 is still less than atmospheric pressure at this point in the method. After backfilling filling chamber 324 with nitrogen gas 346, a dwell or wait time occurs to ensure temperature stabilization of filling chamber 324. The dwell time may vary between 0.25-15 minutes.

Referring now to FIG. 7, after filling chamber 324 is sufficiently saturated, vapor 345 still fills filling chamber 324 as shown in FIG. 7, which is sealed off from tubing network 342 as well as loading and unloading chambers 322, 354. Gas or residual vapor is purged from tubing network 342 via vacuum pump 340 by opening valve 341. Valve 341 is then closed.

Figure 8:
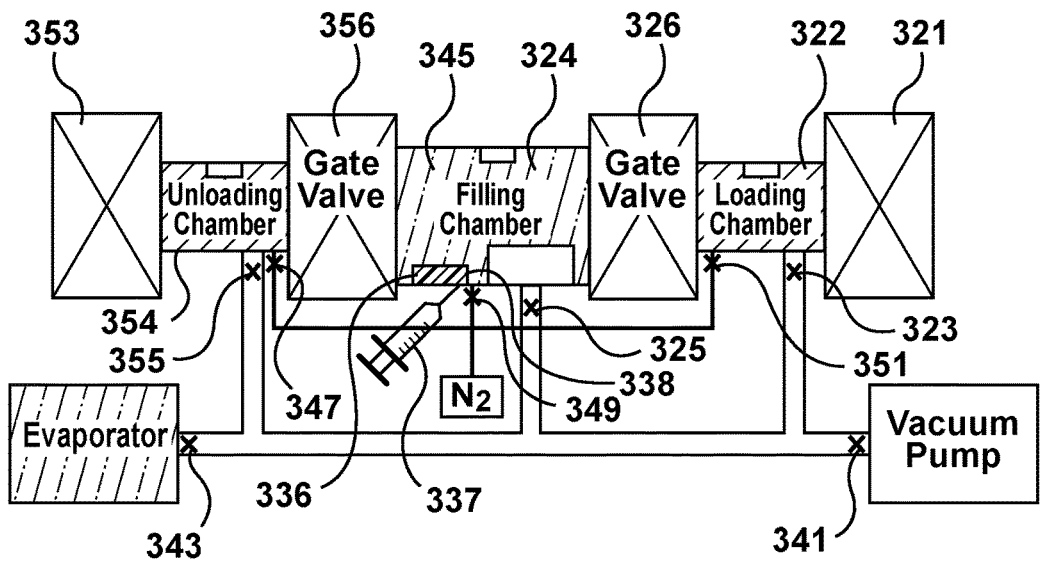
FIG. 8 is a schematic illustration of the apparatus of FIG. 3 being utilized to perform the second step of the flow chart of FIG. 4, wherein a liquid is injected into a container within the filling chamber.
Figure 9:
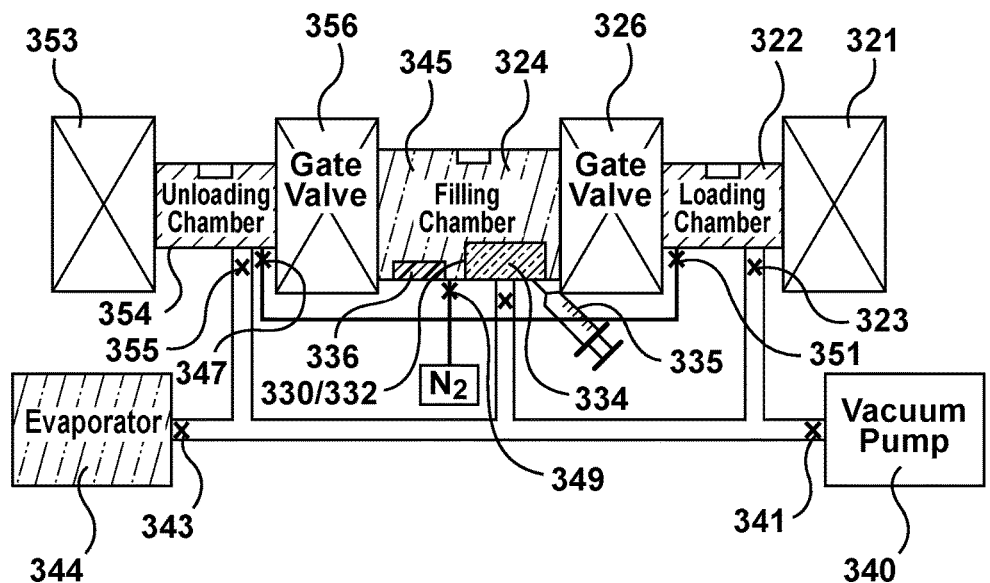
FIG. 9 is a schematic illustration of the apparatus of FIG. 3 being utilized to perform the third step of the flow chart of FIG. 4, wherein a fluid drug formulation is injected into a reservoir including wicking means within the filling chamber.

Turning now to FIG. 8, a second step 464 of method 460 illustrated in FIG. 4 will be described. Second step 464 includes adding liquid 338 into container 336 housed within filling chamber 324. During step 464, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 8, which is now sealed off from tubing network 342 as well as loading and unloading chambers 322, 354. A syringe pump 337 is used to inject liquid 338 into container 336 via a self-sealing opening or port (not shown) formed in filling chamber 324. Liquid 338 which is added into container 336 is selected from the group consisting of the solvent of fluid drug formulation 334, fluid drug formulation 334, or a solution having the same vapor-liquid equilibrium as fluid drug formulation 334 and the same solvent as fluid drug formulation 334. As described above, examples of low capacity drug dissolving solvents include but are not limited to methanol, ethanol, propanol, acetonitrile, ethyl lactate, acetone, and solvent mixtures like tetrahydrofuran/water (9:1 weight ratio). With container 336 filled with liquid 338, any evaporation that may occur within filling chamber 324 during the capillary fill process (i.e., during the remaining steps of method 460) will happen from liquid 338 in container 336. Stated another way, liquid 338 within container 336 provides a supply of solvent vapor for unintended evaporation that may occur during the capillary fill process to prevent evaporation of fluid drug formulation 334 which is added to reservoir 332 in FIG. 9 as described below. Preventing evaporation of fluid drug formulation 334 ensures that there is an adequate supply thereof to fill stents 100 via capillary action and also ensures that there are no changes in concentration or other properties of fluid drug formulation 334. For example, evaporation of fluid drug formulation 334 would include evaporation of the solvent thereof which would result in an undesired increase in the solute concentration thereof, thereby undesirably increasing the mass of solute that fills a fixed volume (i.e. stent 100). After injecting liquid 338 into container 336 via syringe pump 337, a dwell or wait time occurs to ensure saturation of filling chamber 324. The dwell time may vary between 0.25-15 minutes.

Turning now to FIG. 9, a third step 466 of method 460 illustrated in FIG. 4 will be described. Third step 466 includes adding fluid drug formulation 334 into reservoir 332 (which contains wicking means 330) housed within filling chamber 324. During step 466, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 9, which is now sealed off from tubing network 342 as well as loading and unloading chambers 322, 354. A syringe pump 335 is used to inject fluid drug formulation 334 into reservoir 332 via a self-sealing opening or port (not shown) formed in filling chamber 324.

Figure 10:
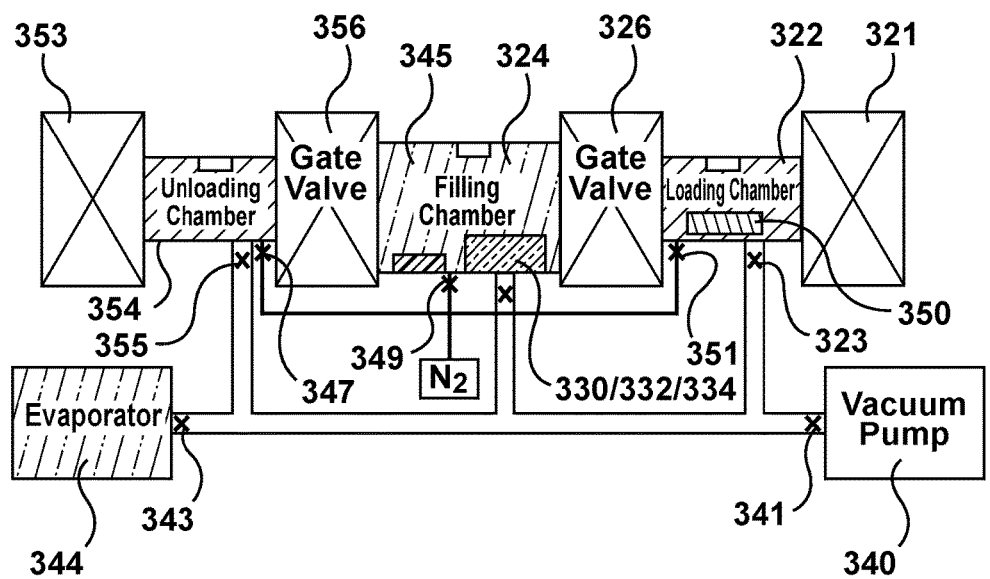
FIG. 10 is a schematic illustration of the apparatus of FIG. 3 being utilized to perform the fourth step of the flow chart of FIG. 4, wherein a stir cover is inserted into a loading chamber of the apparatus.

Turning now to FIGS. 10-15, a fourth step 468 of method 460 illustrated in FIG. 4 will be described. Fourth step 468 includes agitating, stirring, or otherwise mixing/dispersing fluid drug formation 334 and wicking means 330 within reservoir 332. As shown in FIG. 10, a stir cover 350 is inserted or positioned within loading chamber 322 via sealable door 321. More particularly, sealable door 321 is opened and stir cover 350 is moved or transferred into loading chamber while sealable door 321 is opened. Sealable door 321 is then closed. Stir cover 350 is a lid or cover that is configured to be disposed on top of open reservoir 332 to seal or close reservoir 332 into a closed compartment so that the contents thereof may be mixed or agitated without spilling into filling chamber 324 as will be described in more detail herein. After positioning stir cover 350 within loading chamber 322, a preparation cycle may be performed multiple times within loading and unloading chambers 322, 354. The preparation cycle includes removing the gas within loading and unloading chambers 322, 354 and tubing network 342 by opening valve 341 to vacuum pump 340 and then backfilling loading and unloading chambers 322, 354 with nitrogen gas 346 by opening valves 351, 347, respectively, until loading and unloading chambers 322, 354 reach atmospheric pressure or another predetermined or set pressure.

Figure 11:
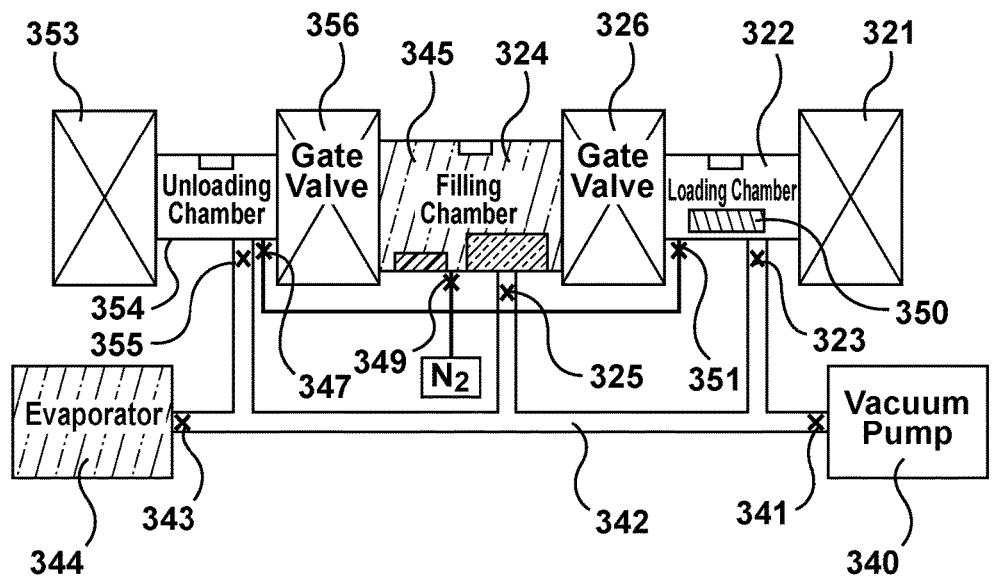
FIG. 11 is a schematic illustration of the apparatus of FIG. 3 being utilized to perform the fourth step of the flow chart of FIG. 4, wherein gas is purged from the loading chamber and an unloading chamber of the apparatus via the vacuum pump.
Figure 12:
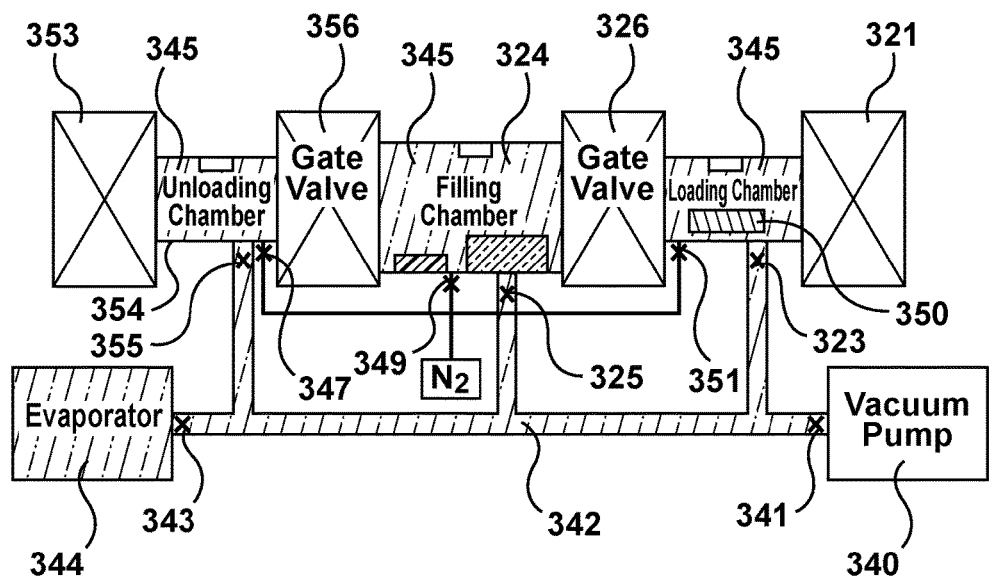
FIG. 12 is a schematic illustration of the apparatus of FIG. 3 being utilized to perform the fourth step of the flow chart of FIG. 4, wherein the loading chamber and the unloading chamber are saturated with solvent vapor.

Once the preparation cycle is repeated as desired, valves 323, 355, 341 are opened such that loading and unloading chambers 322, 354, and vacuum pump 340 respectively, are in fluid communication with tubing network 342, but valve 325 remains closed such that filling chamber 324 is not in fluid communication with tubing network 342. As shown in FIG. 11, gas is purged from loading and unloading chambers 322, 354 and tubing network 342 via vacuum pump 340 to lower the pressure within loading and unloading chambers 322, 354 to a pressure lower than atmospheric pressure. Any residual vapor has now been purged from loading and unloading chambers 322, 354 and tubing network 342 and the pressure in loading and unloading chambers 322, 354 and tubing network 342 may be between 0 PSIA and 14.7 PSIA (0 Torr and 760 Torr). Valve 341 adjacent to vacuum pump 340 is then closed, and valve 343 adjacent to evaporator 344 is subsequently opened so that evaporator 344 is in fluid communication with tubing network 342. With reference to FIG. 12, tubing network 342 and loading and unloading chambers 322, 354 are backfilled with vapor 345 of the solvent of fluid drug formation 334 via evaporator 344 which houses a supply of the vapor. Loading and unloading chambers 322, 354 are saturated with vapor 345 of the solvent of fluid drug formation 334 via evaporator 344 such that loading and unloading chambers 322, 354 reach at or near solvent vapor saturation. Stated another way, loading and unloading chambers 322, 354 are at the vapor-liquid equilibrium of the solvent of fluid drug formulation 334. Although FIGS. 11-12 describe saturation of both loading and unloading chambers 322, 354, only loading chamber 322 is required to reach saturation and undergo the steps shown and described in FIGS. 11-14. After loading and unloading chambers 322, 354 are sufficiently saturated, valves 323, 355, 343 are closed such that loading and unloading chambers 322, 354, and evaporator 344, respectively, are no longer in fluid communication with tubing network 342.

In an embodiment, after backfilling tubing network 342 and loading and unloading chambers 322, 354 with vapor 345 of the solvent of fluid drug formation 334 via evaporator 344, loading and unloading chambers 322, 354 may be backfilled with nitrogen gas 346 by opening valves 351, 347. Nitrogen gas 346 is added to loading and unloading chambers 322, 354 for stabilization thereof. Adding nitrogen gas 346 to loading and unloading chambers 322, 354 enhances stability and prevents temperature fluctuations within the chambers and system when the loading and unloading chambers are saturated with a vapor of the solvent of fluid drug formulation 334 as described above with respect to FIG. 12. Absolute pressure in loading and unloading chambers 322, 354 is still less than atmospheric pressure at this point in the method. Valves 351, 347 are then closed.

Figure 13:
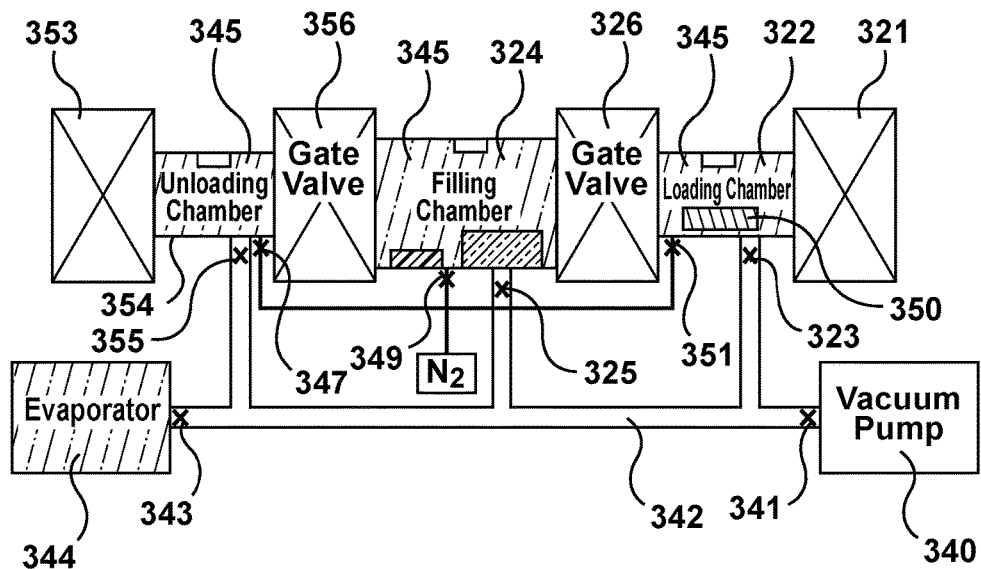
FIG. 13 is a schematic illustration of the apparatus of FIG. 3 being utilized to perform the fourth step of the flow chart of FIG. 4, wherein gas is purged from the network tubing via the vacuum pump.

Referring now to FIG. 13, after loading and unloading chambers 322, 354 are sufficiently saturated, vapor 345 still fills loading and unloading chambers 322, 354 as shown in FIG. 13 which are sealed off from tubing network 342 as well as filling chamber 324 and evaporator 344. Gas or residual vapor is purged from tubing network 342 via vacuum pump 340 by opening valve 341 to purge any residual vapor from tubing network 342.

Figure 14:
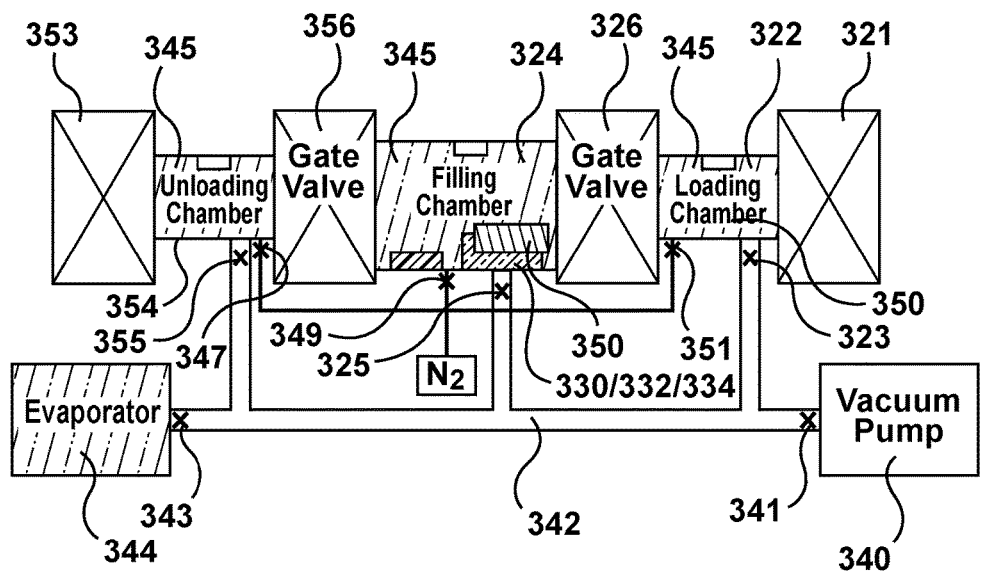
FIG. 14 is a schematic illustration of the apparatus of FIG. 3 being utilized to perform the fourth step of the flow chart of FIG. 4, wherein the stir cover is transferred to the filling chamber and the stir cycle is performed.

Turning now to FIG. 14, with all chambers (loading chamber 322, filling chamber 324, and unloading chamber 354) filled with vapor 345, stir cover 350 is transferred into filling chamber 324. More particularly, first valve gate 326 is opened such that filling chamber 324 and loading chamber 322 are in fluid communication. Stir cover 350 is moved or transferred from loading chamber 322 into filling chamber 324 while first valve gate 326 is opened. Stir cover 350 is positioned over reservoir 332, which includes wicking means 330 and fluid drug formulation 334. First valve gate 326 is then closed such that filling chamber 324 and loading chamber 322 are no longer in fluid communication. As previously described, stir cover 350 is a lid or cover that is configured to be disposed on top of open reservoir 332 to seal or close reservoir 332 into a closed compartment so that wicking means 330 and fluid drug formulation 334 disposed within reservoir 332 may be mixed or agitated without spilling into filling chamber 324. An external vibrator or mixing means (not shown) is utilized to agitate or mix reservoir 332 disposed within filling chamber 324 after stir cover 350 is positioned over reservoir 332. The external vibrator or mixing means agitates filling chamber 324 side to side, as well as up and down, to achieve a fluidized bed of wicking means 330 and fluid drug formulation 334. In an embodiment, the external vibrator is a motor outside of filling chamber 324 and a shaft extends sealingly into filling chamber 324 between the external motor and reservoir 332. In another embodiment hereof, the vibrator or mixing means may be internal to filling chamber 324. After stir cover 350 is positioned or disposed over reservoir 332, the stir cycle commences and mixes or agitates/disperses fluid drug formation 334 and wicking means 330 within reservoir 332 for a predetermined time.

Figure 15:
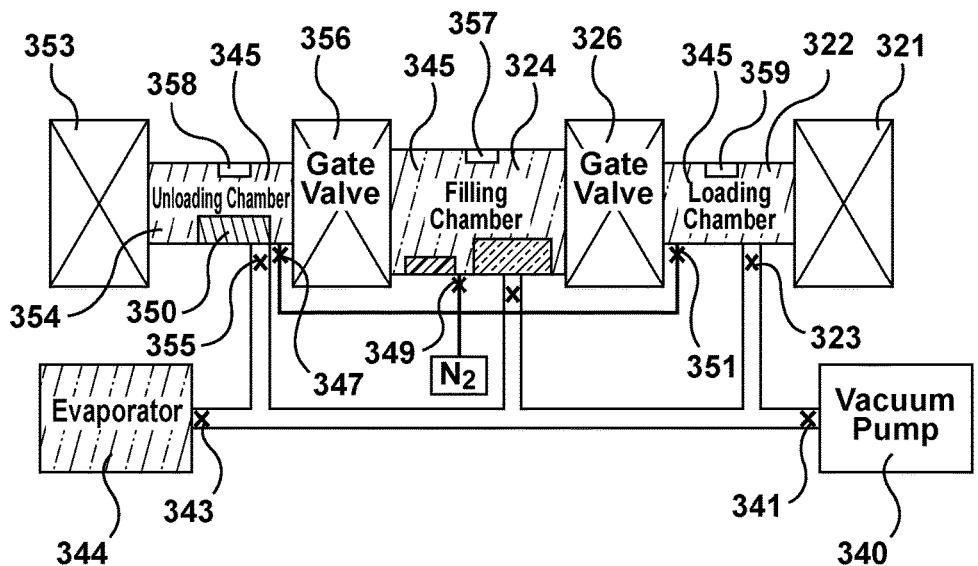
FIG. 15 is a schematic illustration of the apparatus of FIG. 3 being utilized to perform the fourth step of the flow chart of FIG. 4, wherein the stir cover is transferred to the unloading chamber and the loading and unloading chambers are vented.

After the stir cycle is complete, with all chambers (loading chamber 322, filling chamber 324, and unloading chamber 354) filled with vapor 345, stir cover 350 is transferred out of filling chamber 324 as shown in FIG. 15. More particularly, second valve gate 356 is opened such that filling chamber 324 and unloading chamber 354 are in fluid communication. Stir cover 350 is moved or transferred from filling chamber 324 into unloading chamber 354 while second valve gate 356 is opened. Second valve gate 356 is then closed such that filling chamber 324 and unloading chamber 354 are no longer in fluid communication. Vapor 345 is then purged from loading chamber 322 and unloading chamber 354 via respective vents 359, 358, and loading chamber 322 and unloading chamber 354 return to atmospheric pressure. In another embodiment hereof, venting may occur via opening valves 351, 347 to backfill loading and unloading chambers, respectively, with nitrogen from the supply of nitrogen gas 346 to atmospheric pressure. Stir cover 350 may then be removed from unloading chamber 354 via sealable door 353.

Figure 16:
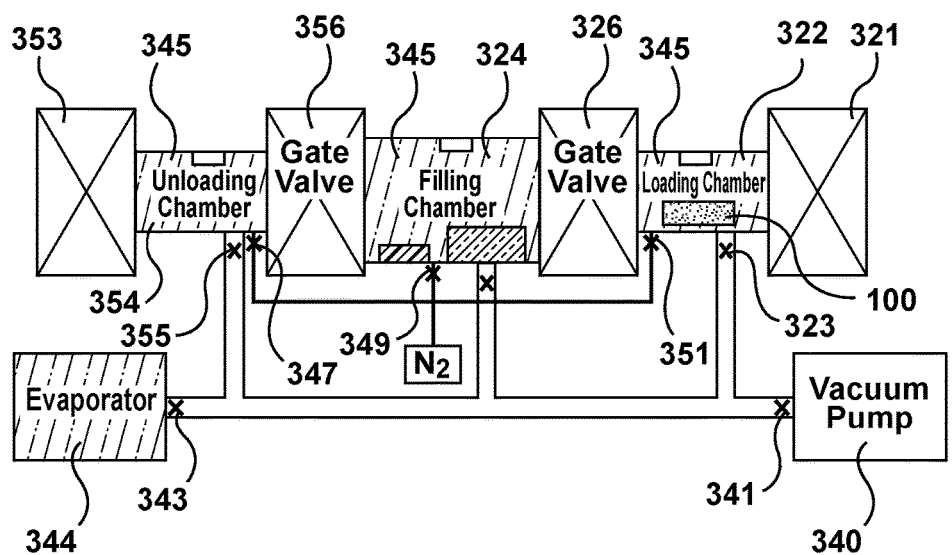
FIG. 16 is a schematic illustration of the apparatus of FIG. 3 being utilized to perform the fifth step of the flow chart of FIG. 4, wherein stents are inserted into the loading chamber.

Turning now to FIG. 16, a fifth step 470 of method 460 illustrated in FIG. 4 will be described. Fifth step 470 includes placing stents 100 into loading chamber 322 via sealable door 321. During step 470, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 16, which is now sealed off from tubing network 342 as well as loading and unloading chambers 322, 354. Stents 100 are held on a manifold or stent suspension means (not shown) which holds or suspends them in place during the capillary filling procedure. Exemplary stent suspension means are described in U.S. patent application Ser. No. 13/457,398 to Peterson et al., filed Apr. 26, 2012, assigned to the same assignee as the present application and herein incorporated by reference in its entirety. The capillary filling procedures in accordance with embodiment hereof may be readily scalable as batch processes. When loaded onto stent suspension means, stents 100 are already formed, that is, hollow wire 102 has previously been shaped or formed into a desired waveform and formed into cylindrical stent 100 as described above with respect to FIG. 1. Alternatively, if desired, the capillary filling process may be performed on straight hollow wires prior to shaping or forming hollow wire 102 into the desired waveform and subsequent stent configuration.

Figure 17:
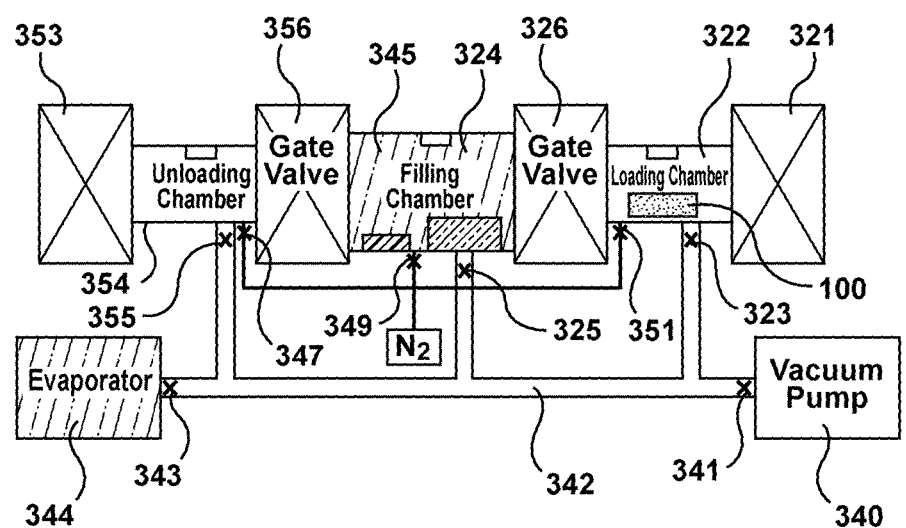
FIG. 17 is a schematic illustration of the apparatus of FIG. 3 being utilized to perform the sixth step of the flow chart of FIG. 4, wherein gas is purged from the loading chamber and an unloading chamber of the apparatus via the vacuum pump.
Figure 18:
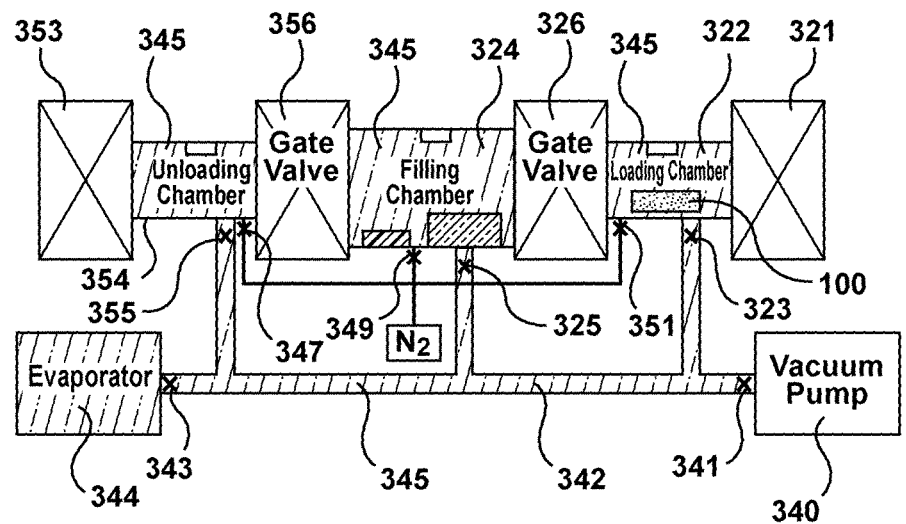
FIG. 18 is a schematic illustration of the apparatus of FIG. 3 being utilized to perform the sixth step of the flow chart of FIG. 4, wherein the loading chamber and the unloading chamber are saturated with solvent vapor and then gas is purged from the network tubing via the vacuum pump.

Turning now to FIGS. 17-18, a sixth step 472 of method 460 illustrated in FIG. 4 will be described. Sixth step 472 includes causing loading and unloading chambers 322, 354 to reach the vapor-liquid equilibrium of the solvent of fluid drug formulation 334. With reference to FIG. 17, valves 323, 355, 341 are opened such that loading and unloading chambers 322, 354, and vacuum pump 340, respectively, are in fluid communication with tubing network 342, but valve 325 remains closed such that filling chamber 324 is not in fluid communication with tubing network 342. As shown in FIG. 17, the gas within loading and unloading chambers 322, 354 and tubing network 342 is purged by opening valve 341 to vacuum pump 340 to lower the pressure within loading and unloading chambers 322, 354 to a pressure lower than atmospheric pressure. Any residual vapor has now been purged from loading and unloading chambers 322, 354 and tubing network 342 and the pressure in loading and unloading chambers 322, 354 and tubing network 342 may be between 0 PSIA and 14.7 PSIA (0 Torr and 760 Torr). Valve 341 is then closed. With reference to FIG. 18, tubing network 342 and loading and unloading chambers 322, 354 are backfilled with vapor 345 of the solvent of fluid drug formation 334 by opening valve 343 to evaporator 344 which houses a supply of the vapor. Loading and unloading chambers 322, 354 are saturated with vapor 345 of the solvent of fluid drug formation 334 via evaporator 344 such that loading and unloading chambers 322, 354 reach solvent vapor saturation. Stated another way, loading and unloading chambers 322, 354 are at the vapor-liquid equilibrium of the solvent of fluid drug formulation 334. After loading and unloading chambers 322, 354 are sufficiently saturated, valves 323, 355, 343 are closed such that loading and unloading chambers 322, 354, and evaporator 344, respectively, are no longer in fluid communication with tubing network 342.

In an embodiment, after backfilling tubing network 342 and loading and unloading chambers 322, 354 with vapor 345 of the solvent of fluid drug formation 334 via evaporator 344, loading and unloading chambers 322, 354 may be backfilled with nitrogen gas 346 by opening valves 351, 347 for stabilization of loading and unloading chambers 322, 354. Adding nitrogen gas 346 to loading and unloading chambers 322, 354 enhances stability and prevents temperature fluctuations within the chamber and system when the loading and unloading chambers are saturated with a vapor of the solvent of fluid drug formulation 334 as described above with respect to FIG. 18. Absolute pressure in loading and unloading chambers 322, 354 is still less than atmospheric pressure at this point in the method. After backfilling loading and unloading chambers 322, 354 with nitrogen gas 346, a dwell or wait time occurs to ensure temperature stabilization of loading and unloading chambers 322, 354. The dwell time may vary between 0.25-15 minutes. Vapor 345 still fills loading and unloading chambers 322, 354, which are sealed off from tubing network 342 as well as filling chamber 324. Gas or residual vapor is purged from tubing network 342 via vacuum pump 340 by opening valve 341.

Figure 19:
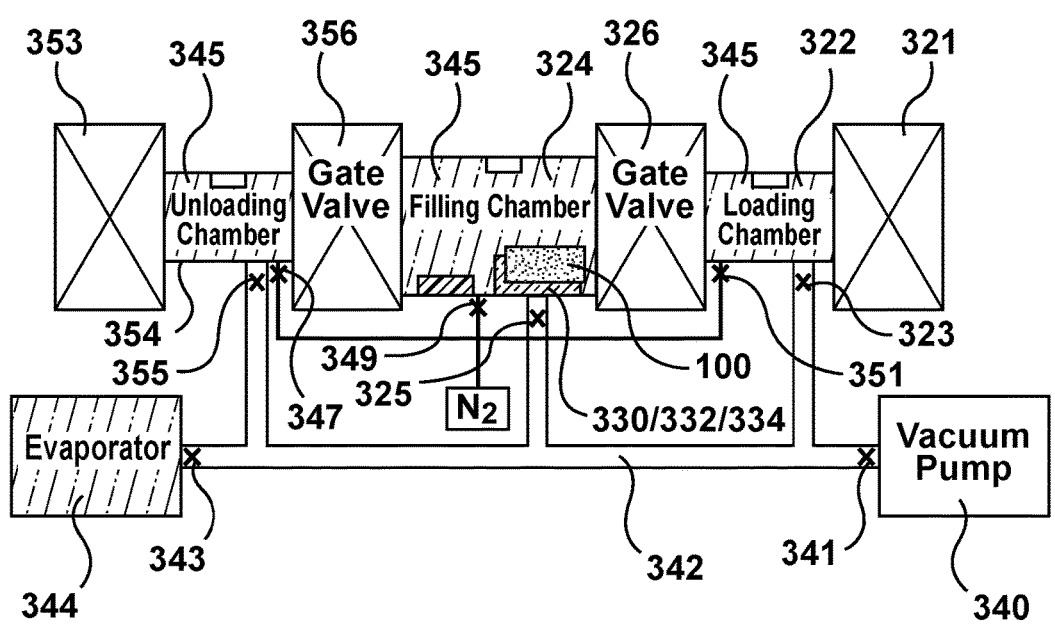
FIG. 19 is a schematic illustration of the apparatus of FIG. 3 being utilized to perform the seventh step of the flow chart of FIG. 4, wherein the stents are transferred into the filling chamber.

Turning now to FIG. 19, a seventh step 474 of method 460 illustrated in FIG. 4 will be described. Seventh step 474 includes transferring stents 100 into filling chamber 324. During step 474, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills all chambers (loading chamber 322, filling chamber 324, and unloading chamber 354) as shown in FIG. 19. First valve gate 326 is opened such that filling chamber 324 and loading chamber 322 are in fluid communication. Stents 100 are moved or transferred from loading chamber 322 into filling chamber 324 while first valve gate 326 is opened. First valve gate 326 is then closed such that filling chamber 324 and loading chamber 322 are no longer in fluid communication. First valve gate 326 sealingly closes around the stent suspension means which are holding stents 100.

Figure 20:
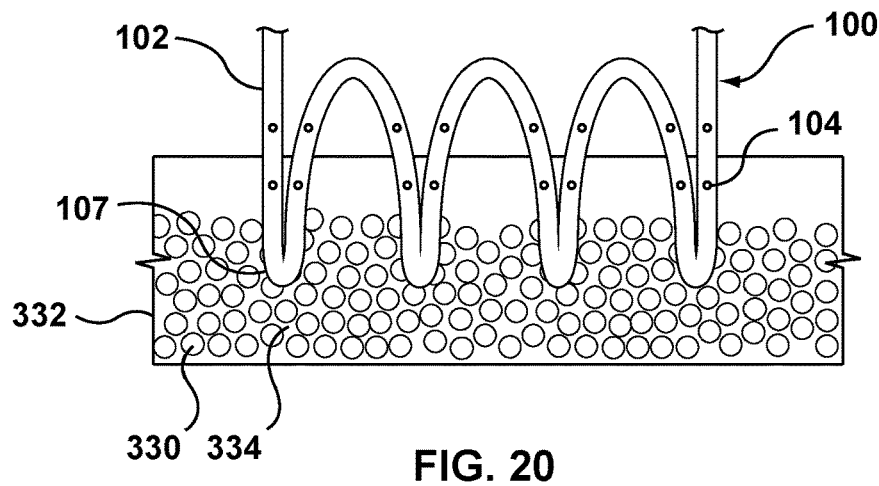
FIG. 20 is a schematic illustration of a portion of a stent in position with respect to the wicking means to perform the eighth step of the flow chart of FIG. 4, wherein the stent is suspended in a vertical orientation.
Figure 21:
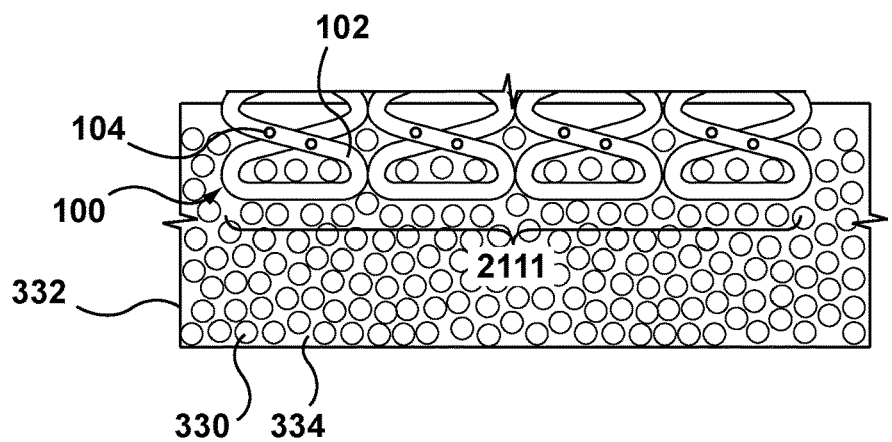
FIG. 21 is a schematic illustration of a portion of a stent in position with respect to the wicking means to perform the eighth step of the flow chart of FIG. 4, wherein the stent is suspended in a horizontal orientation.
Figure 22:
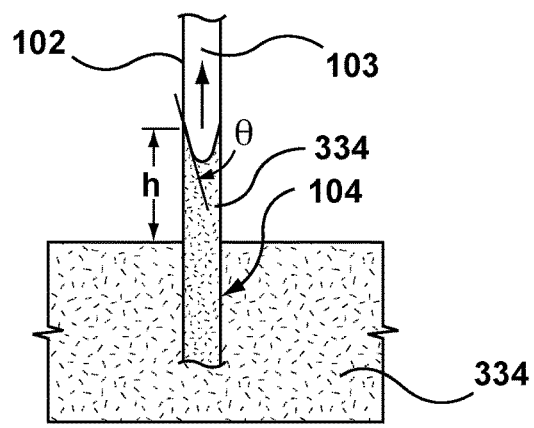
FIG. 22 is a schematic illustration of a portion of a stent performing the eighth step of the flow chart of FIG. 4, wherein the fluid drug formulation fills a lumen of the hollow wire of the stent via capillary action.

Turning now to FIGS. 20-22, an eighth step 476 of method 460 illustrated in FIG. 4 will be described. Eighth step 476 includes filling stents 100 via capillary action. During step 476, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. As shown in FIGS. 21 and 22, at least a portion of stent 100 is first positioned or placed into contact with wicking means 330 housed within reservoir 332. At least one of the plurality of side openings 104, or first or second ends 114, 114' of hollow wire 102, must be in contact with wicking means 330. However, in an embodiment hereof, stent 100 may be entirely submersed or otherwise placed into contact with wicking means 330. Stents 100 may be suspended by stent suspension means in a vertical orientation as shown in FIG. 20, or alternatively may suspend stents 100 in a horizontal orientation as shown in FIG. 21. Notably, only a portion of each stent having at least one side hole or port 104 is required to be submersed into wicking means 330. As such, a minimal amount of the exterior surfaces of wires 102 of stents 100 are exposed to the fluid drug formulation and most of the exterior surface of the hollow wire of the stent is never exposed to the fluid drug formulation, therefore not requiring additional cleaning or removal of drug residue. When held vertically as shown in FIG. 20, only a tip 107 of each stent 100 is submersed into wicking means 330 such that at least one side hole 104 is in contact with wicking means 330 and exposed to fluid drug formulation 334. For example, in an embodiment, approximately 0.3 mm of the length of each stent is exposed or driven into to the wicking means. When held horizontally as shown in FIG. 21, a longitudinal strip or segment 2111 along an outer surface of each stent 100 is submersed into wicking means 330 such that at least one side hole 104 is in contact with wicking means 330 and exposed to fluid drug formulation 334.

As shown in both FIGS. 20 and 21, wicking means 330 is a plurality of beads within the layer of fluid drug formulation 334 contained within reservoir 332. In an embodiment, the beads of wicking means 330 may be a type of ceramic beads between 0.3 mm and 1.5 mm in diameter. Other suitable materials for the beads of wicking means 330 include glass, or metal such as steel, aluminum, titanium, or stainless steel. The individual size of the beads, as well as the height of the layer of beads, may vary according to application. The beads minimize the contact area between stents 100 and fluid drug formulation 334 to control surface energy properties during the filling procedure. In an embodiment, the layer of fluid drug formulation is approximately the same height as the layer of beads. However, in another embodiment, the layer of beads has a greater height than the layer of fluid drug formulation such that a layer of "dry" beads extend over the "wet" beads that are submersed in the layer of fluid drug formulation. The layer of "dry" beads provides additional cleaning of the exterior surfaces of stents 100 when stents 100 are retracted out of the beads. Although wicking means embodiments described herein may be shown with only one stent 100, it will be understood by one of ordinary skill in the art that any wicking means described herein may accommodate a plurality of stents 100. Other described as a plurality of ceramic beads, other wicking means described in U.S. patent application Ser. No. 13/457,398, previously incorporated by reference, may be used such as but not limited to an open-celled polyurethane sponge or foam.

After stents 100 are positioned or placed into contact with wicking means 330, stents 100 are allowed or permitted to fill via capillary action. Wicking means 330 is in contact with fluid drug formulation 334, to control transfer of the fluid drug formulation into lumen 103 of hollow wire 102 of stent 100. Wicking means 330 transfer fluid drug formulation 334 from reservoir 332 into submersed holes 104 of stent 100. Lumen 103 of hollow wire 102 of stent 100 is filled by surface tension driving fluid drug formulation 334 through the stent lumen, until the entire length of lumen 103 is filled via capillary action forces. During the filling step, filling chamber 324 is maintained at or near the vapor-liquid equilibrium of the solvent of fluid drug formulation 334 such that evaporation does not precipitate therapeutic substance or drug 112 as fluid drug formulation 334 fills lumen 103 of hollow wire 102 of stents 100.

FIG. 22 is a schematic illustration of a portion of a stent 100 submersed or in contact with wicking means 330 to demonstrate the capillary filling process. Fluid drug formulation 334 passes through hole(s) 104 on hollow wire 102 that are in contact with wicking means 330 as shown in FIG. 22, which illustrates only a portion of hollow wire 102 having a side hole 104 submersed into wicking means 330. Fluid drug formulation 334 forms a concave meniscus within lumen 103 of hollow wire 102. Adhesion forces pull fluid drug formulation 334 up until there is a sufficient mass of fluid drug formulation 334 present for gravitational forces to overcome the intermolecular forces between fluid drug formulation 334 and hollow wire 102, or the advancing fluid column completely fills the lumen. The height h of a column of fluid drug formulation 334 is determined by $$h = \frac{2\gamma\cos\theta}{\rho g r},$$

where $\gamma$ is the liquid-air surface tension (force/unit length), $\theta$ is the contact angle, $\rho$ is the density of fluid drug formulation 334 (mass/volume), g is local gravitational field strength (force/unit mass), and r is the radius of hollow wire 102 (length). Due to the nature of capillary filling and the intermolecular forces between fluid drug formulation 334 and hollow wire 102, fluid drug formulation 334 does not exit or leak out of non-submersed holes or ports 104 that occur along the length of the stent as fluid drug formulation 334 fills lumen 103 of hollow wire 102.

The time required to fill the entire length of lumen 103 of hollow wire 102 of stent 100 depends upon the stent configuration and length. Fill time depends upon various factors, including but not limited to the length of hollow wire 102, the size of holes 104, the number of submersed holes 104, the size of lumen 103, and the properties of wicking means 330 and fluid drug formulation 334. For example, in an embodiment in a horizontally-oriented 3 mm×18 mm stent is placed into contact with wicking means 330, which is in contact with a fluid drug formulation including rapamycin dissolved in methanol, filling time is approximately 60 seconds. If it is desired to reduce the overall fill time, the number of submersed holes 104 may be increased. Often, horizontal orientation of stents may be utilized if it is desired to place a greater number of side holes into contact with the wicking means and thereby reduce the overall fill time. Contact is maintained between wicking means 330 and stent 100 until lumenal space 103 of hollow wire 102 is at least partially filled with fluid drug formulation 334 via capillary action.

After lumen 103 is completely filled, or partially filled if so desired, stents 100 are retracted or pulled up such that stents 100 are no longer in contact with wicking means 330 but is located within filling chamber 324. As stents 100 are retracted out of wicking means 330, wicking means 330 removes excess fluid drug formulation 334 from the exterior surfaces of wires 102 of stents 100 such that stents 100 are free or substantially free of drug residue on their exterior surfaces, leaving fluid drug formulation 334 only within lumen 103 of hollow wire 102 of stent 100. During retraction of stents 100, the beads of wicking means 330 pull or remove excess fluid drug formulation from the exterior surfaces of hollow wires 102 of stents 100.

Figure 23:
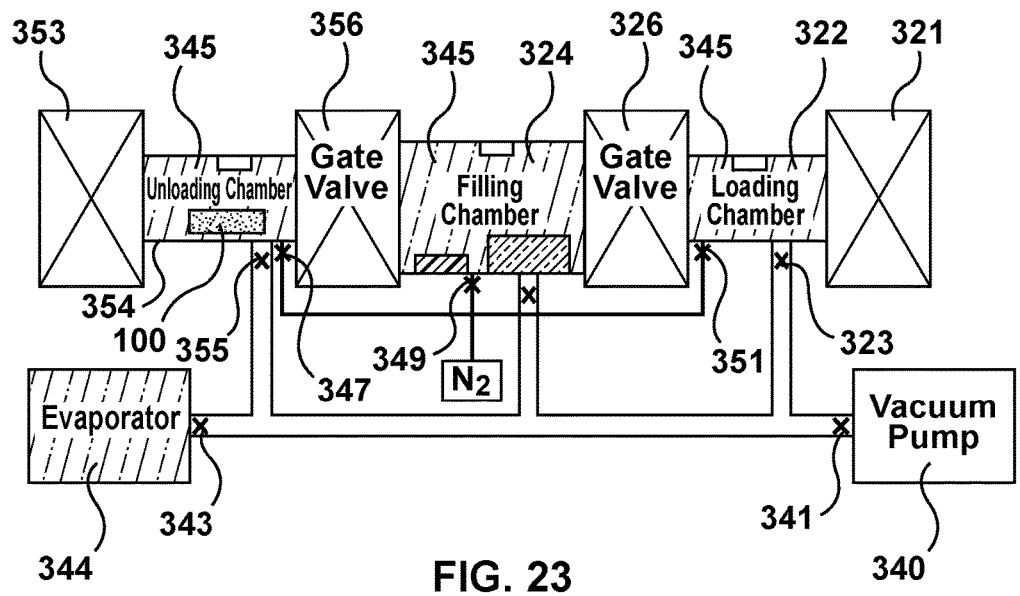
FIG. 23 is a schematic illustration of the apparatus of FIG. 3 being utilized to perform the ninth step of the flow chart of FIG. 4, wherein the stents are transferred to the unloading chamber after being filled via capillary action.

Turning now to FIG. 23, a ninth step 478 of method 460 illustrated in FIG. 4 will be described. Ninth step 478 includes transferring stents 100 into unloading chamber 354. During step 478, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills all chambers (loading chamber 322, filling chamber 324, and unloading chamber 354) as shown in FIG. 23. Second valve gate 356 is opened such that filling chamber 324 and unloading chamber 354 are in fluid communication. Stents 100 are moved or transferred from filling chamber 324 into unloading chamber 354 while second valve gate 356 is opened. Second valve gate 356 is then closed such that filling chamber 324 and unloading chamber 354 are no longer in fluid communication.

Figure 24:
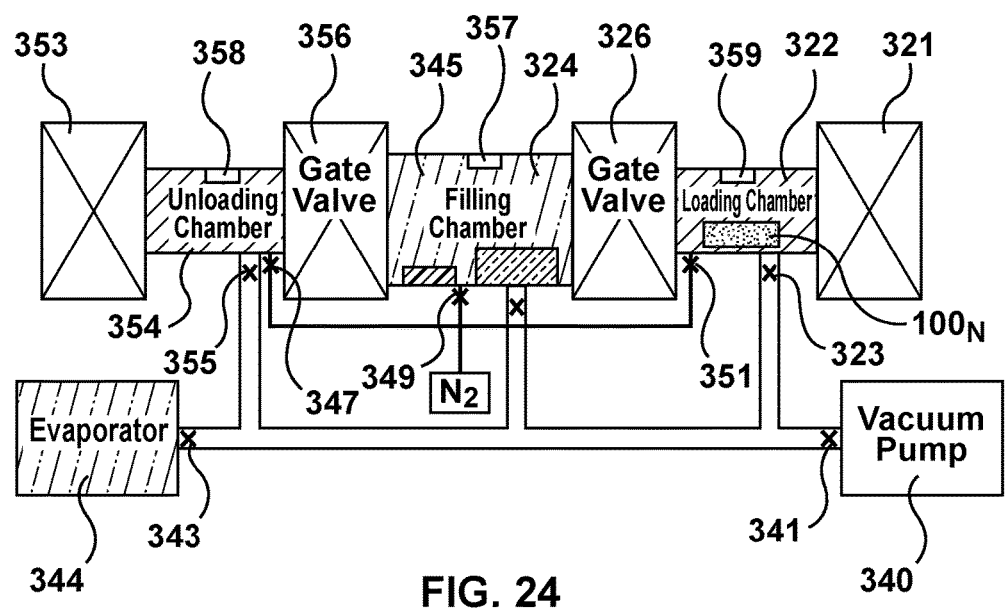
FIG. 24 is a schematic illustration of the apparatus of FIG. 3 being utilized to perform the tenth and eleventh step of the flow chart of FIG. 4, wherein a therapeutic substance of the fluid drug formulation is precipitated within the lumen of the hollow wire of the stent and an additional or subsequent batch of stents to be filled via capillary action is inserted into the loading chamber.

With continued reference to FIG. 23, a tenth step 480 of method 460 illustrated in FIG. 4 will be described. Tenth step 480 includes reducing a solvent vapor pressure in unloading chamber 354 to evaporate the solvent of fluid drug formulation 334 after stents 100 have been transferred into unloading chamber 354. During step 480, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 24, which is now sealed off from tubing network 342 as well as loading and unloading chambers 322, 354. More particularly, during step 480, stents 100 are still positioned within unloading chamber 354 and vapor 345 is purged from loading chamber 322 and unloading chamber 354 via respective vents 359, 358, so that loading chamber 322 and unloading chamber 354 return to atmospheric pressure. Stated another way, loading chamber 322 and unloading chamber 354 are vented via respective vents 359, 358 to reduce their solvent vapor pressure and to increase overall pressure back to ambient conditions. In another embodiment hereof, venting may occur via opening valves 351, 347 to backfill loading and unloading chambers, respectively, with nitrogen from the supply of nitrogen gas 346. As the solvent vapor pressure is reduced in loading chamber 322 and unloading chamber 354, evaporation of fluid drug formulation 334 within lumen 103 of hollow wire 102 is initiated and the solvent of drug fluid formulation 334 is removed, thereby precipitating its constituents. After the solvent or dispersion medium is removed from lumen 103, therapeutic substance or drug 112 fills at least a portion of lumen 103. Thus, extracting the solvent or dispersion medium of fluid drug formulation 334 from within the lumen 103 of hollow wire 102 thus precipitates the solute, i.e., therapeutic substance or drug 112, within lumen 103 and creates a drug-filled stent 100 with primarily only therapeutic substance or drug 112 and one or more excipients within stent 100 to be eluted into the body. After evaporation of fluid drug formulation 334, filled stents 100 may be removed from unloading chamber 354 of apparatus 320.

The next batch of unfilled stents $100_N$ may then be inserted or positioned into loading chamber 322 of apparatus 320 for filling thereof as shown in FIG. 24 and according to eleventh step 482 of method 460. Since vapor 345 still fills filling chamber 324, additional batches of stents may be filled with the same fluid drug formulation without concentration changes. More particularly, the first four steps of method 460 (steps 462, 464, 466, 468) described above with respect to FIGS. 5-15 do not need to be repeated for subsequent additional batches of stents that are to be filled. Rather, the method of filling subsequent additional batches of stents pick up at FIG. 16 with the next batch of stents being positioned or placed into loading chamber 322.

Although method 460 is described above with respect to apparatus 320, method 460 may alternatively be carried out on an apparatus having only a filling chamber and a loading chamber. Stated another way, the method steps performed in the unloading chamber may alternatively take place within the loading chamber. As such, apparatus 320 is only required to have two distinct, air-locked chambers, namely a filling chamber and a loading/unloading chamber.

Alternative Method of Capillary Filling with Apparatus 320

FIGS. 25-44 illustrate an alternative method of using apparatus 320 for capillary filling of multiple, sequential batches of stents in a timely or effective manner. The alternative method illustrated in FIGS. 25-44 essentially utilizes both loading and unloading chambers 322, 354 as loading chambers that receive different components (i.e., the stir cover and the stents) at the same time in order to reduce the total time required for the capillary fill process and thus increase efficiency thereof. In addition, as will be described in more detail herein, by utilizing loading and unloading chambers 322, 354 simultaneously, the number of total steps required in the alternative method of use is reduced as compared to the method of use described above.

Figure 25:
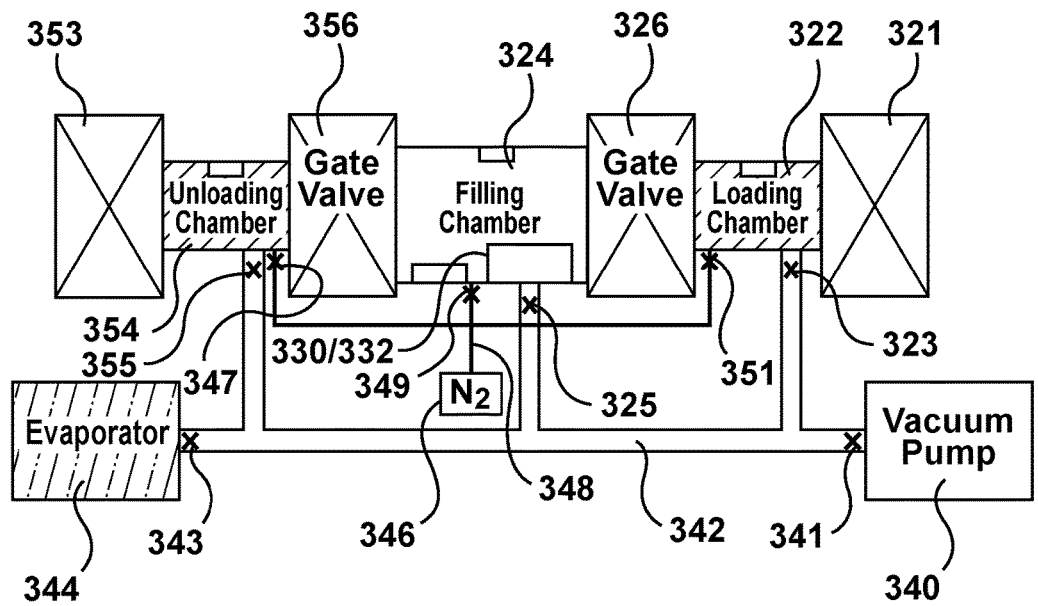
FIG. 25 is a schematic illustration of the apparatus of FIG. 3 being utilized to perform an alternative method of filling multiple batches of stents via capillary action, wherein gas is purged from the filling chamber of the apparatus via the vacuum pump.
Figure 26:
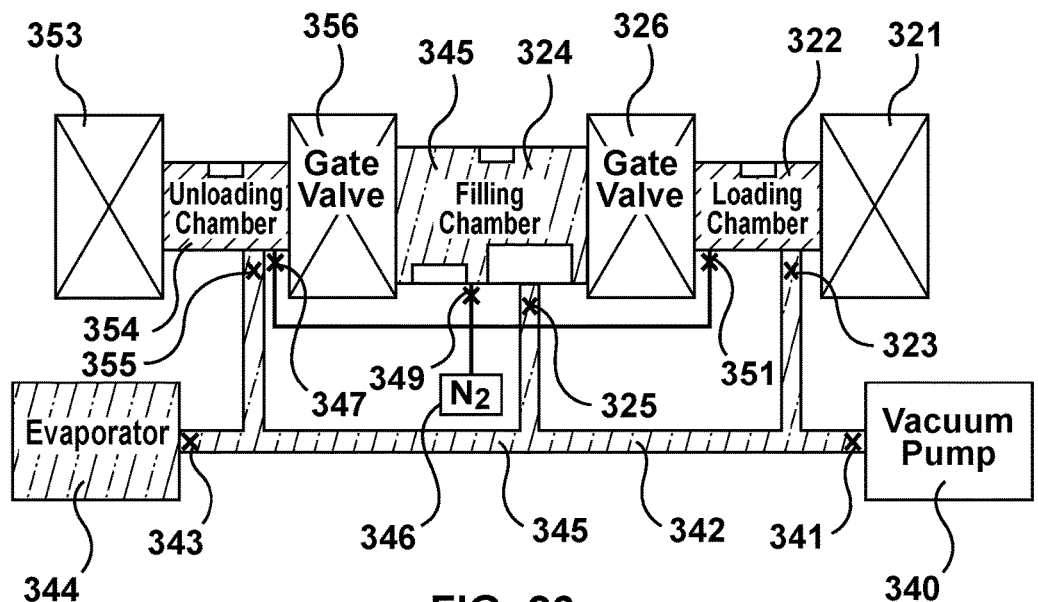
FIG. 26 is a schematic illustration of the apparatus of FIG. 3 being utilized to perform an alternative method of filling multiple batches of stents via capillary action, wherein the filling chamber is saturated with solvent vapor.
Figure 27:
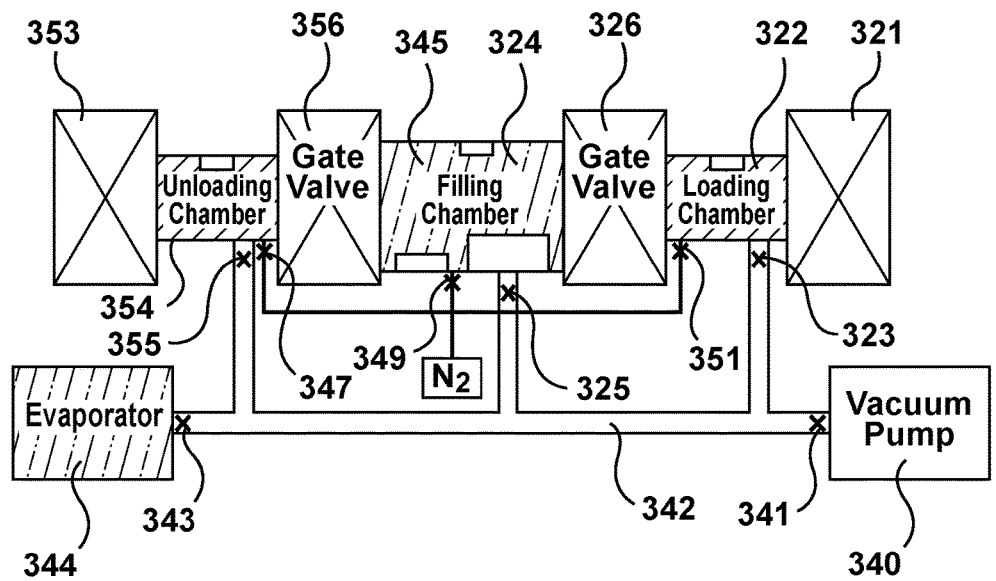
FIG. 27 is a schematic illustration of the apparatus of FIG. 3 being utilized to perform an alternative method of filling multiple batches of stents via capillary action, wherein gas is purged from the network tubing of the apparatus via the vacuum pump.

FIGS. 25-27 illustrate the first or initial step of the alternative method. The initial step of the alternative method of use is similar to method step 462 described above, and includes causing filling chamber 324 to reach a vapor-liquid equilibrium of a solvent of fluid drug formulation 334. As such, FIGS. 25-27 are the same as FIGS. 5-7 and illustrate filling chamber 324 reaching a vapor-liquid equilibrium of a solvent of fluid drug formulation 334. For sake of completeness a brief description of method step 462 is repeated herein. Prior to the initiation of the method, both first and second valve gates 326, 356 are closed such that filling chamber 324, loading chamber 322, and unloading chamber 354 are distinct or separate closed chambers and are not in fluid communication with each other. Valve 325 is open such that filling chamber 324 is in fluid communication with tubing network 342, but valves 323, 355 are closed such that loading and unloading chambers 322, 354, respectively, are not in fluid communication with tubing network 342. As described above, initially a preparation cycle may be performed multiple times within filling chamber 324. The preparation cycle includes removing the gas within filling chamber 324 and tubing network 342 by opening valve 341 to vacuum pump 340 and then backfilling filling chamber 324 with nitrogen gas 346 by opening valve 349 until filling chamber 324 reaches atmospheric pressure or another predetermined or set pressure. Once the preparation cycle is repeated as desired, the gas within filling chamber 324 and tubing network 342 is purged by opening valve 341 to vacuum pump 340 to lower the pressure within filling chamber 324 to a pressure lower than atmospheric pressure as shown in FIG. 25. Any residual vapor has now been purged from filling chamber 324 and the pressure in filling chamber 324 and tubing network 342 may be between 0 PSIA and 14.7 PSIA (0 Torr and 760 Torr). Valve 341 is then closed. With reference to FIG. 26, tubing network 342 and filling chamber 324 are now backfilled with a vapor 345 of the solvent of fluid drug formation 334 by opening valve 343 to evaporator 344 which houses a supply of the solvent vapor. Filling chamber 324 is saturated with vapor 345 of the solvent of fluid drug formation 334 via evaporator 344 such that filling chamber 324 reaches solvent vapor saturation. Stated another way, filling chamber 324 is at the vapor-liquid equilibrium of the solvent of fluid drug formulation 334. Valves 343, 325 are then closed.

In an embodiment, after backfilling tubing network 342 and filling chamber 324 with vapor 345 of the solvent of fluid drug formation 334 via evaporator 344, filling chamber 324 may be backfilled with nitrogen gas 346 by opening valve 349 for stabilization of filling chamber 324. Adding nitrogen gas 346 to filling chamber 324 enhances stability and prevents temperature fluctuations within the chamber and system when the filling chamber is saturated with a vapor of the solvent of fluid drug formulation 334 as described above with respect to FIG. 26. Absolute pressure in filling chamber 324 is still less than atmospheric pressure at this point in the method. After backfilling filling chamber 324 with nitrogen gas 346, a dwell or wait time occurs to ensure temperature stabilization of filling chamber 324. The dwell time may vary between 0.25-15 minutes.

After filling chamber 324 is sufficiently saturated, vapor 345 still fills filling chamber 324, which is sealed off from tubing network 342 as well as loading and unloading chambers 322, 354. Gas or residual vapor within tubing network 342 is purged via vacuum pump 340 by opening valve 341 as shown in FIG. 27.

Figure 28:
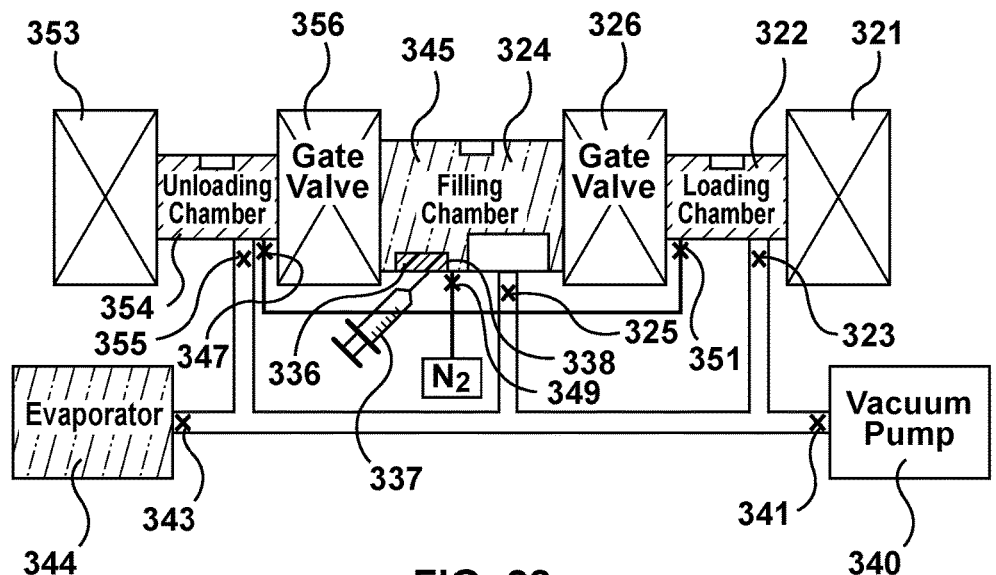
FIG. 28 is a schematic illustration of the apparatus of FIG. 3 being utilized to perform an alternative method of filling multiple batches of stents via capillary action, wherein a liquid is injected into a container within the filling chamber.

FIG. 28 illustrates the second step of the alternative method. The second step of the alternative method of use is similar to method step 464 described above, and includes adding liquid 338 into container 336 housed within filling chamber 324. As such, FIG. 28 is similar to FIG. 8 and illustrates liquid 338 being added to container 336. For sake of completeness a brief description of method step 464 is repeated herein. During this step, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 28, which is now sealed off from tubing network 342 as well as loading and unloading chambers 322, 354. Syringe pump 337 is used to inject liquid 338 into container 336 via a self-sealing opening or port (not shown) formed in filling chamber 324. After injecting liquid 338 into container 336, a dwell or wait time occurs to ensure saturation of filling chamber 324. The dwell time may vary between 0.25-15 minutes.

Figure 29:
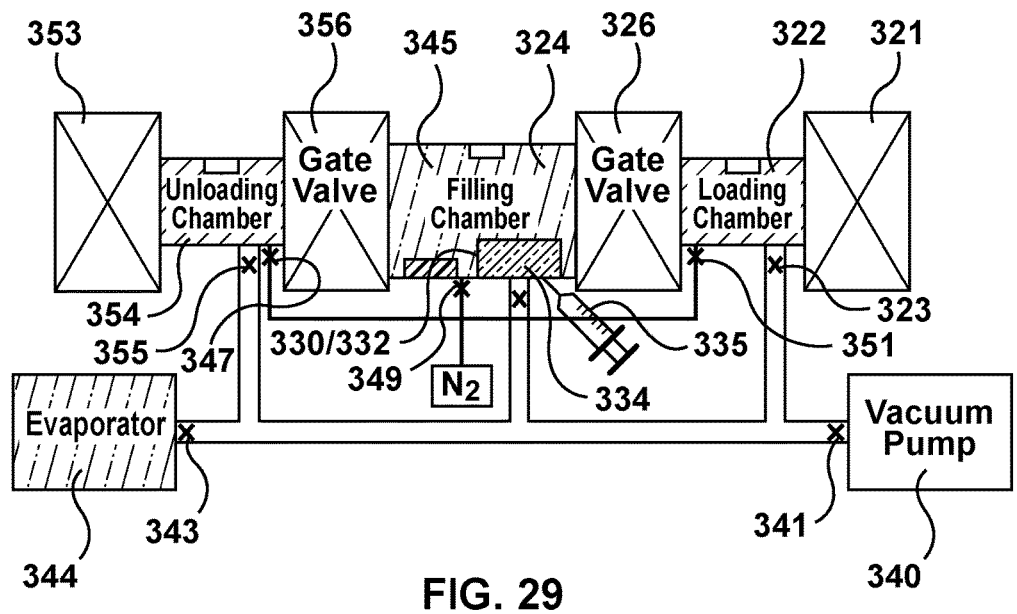
FIG. 29 is a schematic illustration of the apparatus of FIG. 3 being utilized to perform an alternative method of filling multiple batches of stents via capillary action, wherein a fluid drug formulation is injected into a reservoir including wicking means within the filling chamber.

FIG. 29 illustrates the third step of the alternative method. The third step of the alternative method of use is similar to method step 466 described above, and includes adding fluid drug formulation 334 into reservoir 332 (which contains wicking means 330) housed within filling chamber 324. As such, FIG. 29 is similar to FIG. 9 and illustrates fluid drug formulation 334 being added into reservoir 332. For sake of completeness a brief description of method step 466 is repeated herein. During this step, both first and second valve gates 326, 356 remain closed such that filling chamber 324, loading chamber 322, and unloading chamber 354 are distinct or separate closed chambers and are not in fluid communication with each other. In addition, valves 323, 325, 355 are closed such that loading, filling, and unloading chambers 322, 324, 354, respectively, are not in fluid communication with tubing network 342. Valves 351, 349, 347 are also closed such that loading, filling, and unloading chambers 322, 324, 354, respectively, are not in fluid communication with the supply of nitrogen gas 346. Further, valves 341, 343 are also preferably closed since vacuum pump 340 and evaporator 344 are not in use. Vapor 345 still fills filling chamber 324 as shown in FIG. 29, which is now sealed off from tubing network 342 as well as loading and unloading chambers 322, 354. Syringe pump 335 is used to inject fluid drug formulation 334 into reservoir 332 via a self-sealing opening or port (not shown) formed in filling chamber 324.

Figure 30:
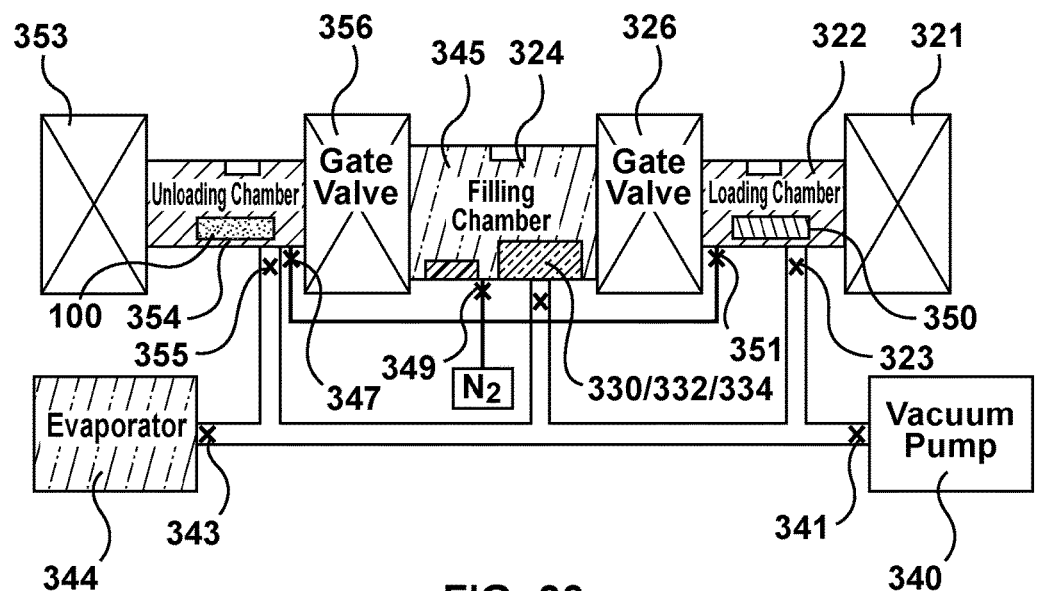
FIG. 30 is a schematic illustration of the apparatus of FIG. 3 being utilized to perform an alternative method of filling multiple batches of stents via capillary action, wherein a stir cover is inserted into a loading chamber of the apparatus.

FIGS. 30-35 illustrate the fourth step of the alternative method. The fourth step of the alternative method of use deviates from the previous method and illustrates how unloading both loading and unloading chambers 322, 354 as loading chambers that receive different components (i.e., stir cover 350 and a first batch of stents 100) at the same time in order to reduce the total time required for the capillary fill process and thus increase efficiency thereof. The fourth step of the alternative method still includes mixing fluid drug formulation 334 and wicking means 330 within reservoir 332 as described above with respect to fourth step 468, but the fourth step of the alternative method combines step 468 and step 470 into one step and further eliminates the need for step 472 described above in which the loading chamber is caused to reach vapor-equilibrium again after loading stents 100 therein. More particularly, as shown in FIG. 30, a stir cover 350 is inserted or positioned within loading chamber 322 via sealable door 321 and a first batch of stents 100 is positioned in unloading chamber 354 via sealable door 353. After positioning stir cover 350 within loading chamber 322 and the first batch of stents 100 within unloading chamber 354, a preparation cycle may be performed multiple times within loading and unloading chambers 322, 354. The preparation cycle includes removing the gas within loading and unloading chambers 322, 354 and tubing network 342 by opening valve 341 to vacuum pump 340 and then backfilling loading and unloading chambers 322, 354 with nitrogen gas 346 by opening valves 351, 347, respectively, until loading and unloading chambers 322, 354 reach atmospheric pressure or another predetermined or set pressure.

Figure 31:
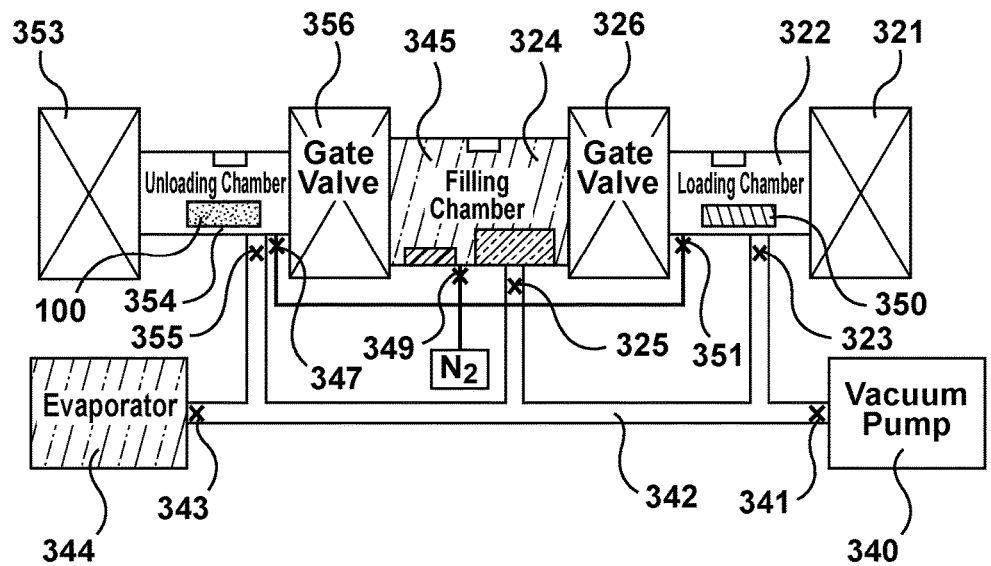
FIG. 31 is a schematic illustration of the apparatus of FIG. 3 being utilized to perform an alternative method of filling multiple batches of stents via capillary action, wherein gas is purged from the loading chamber of the apparatus via the vacuum pump.

Next, with reference to FIG. 31, valves 323, 355 are opened such that loading and unloading chambers 322, 354, respectively, are in fluid communication with tubing network 342, but valve 325 remains closed such that filling chamber 324 is not in fluid communication with tubing network 342. Gas is purged from loading and unloading chambers 322, 354 and tubing network 342 by opening valve 341 to vacuum pump 340 to lower the pressure within loading and unloading chambers 322, 354 to a pressure lower than atmospheric pressure. Any residual vapor has now been purged from loading and unloading chambers 322, 354 and the pressure in loading and unloading chambers 322, 354 and tubing network 342 may be between 0 PSIA and 14.7 PSIA (0 Torr and 760 Torr). Valve 341 is then closed.

Figure 32:
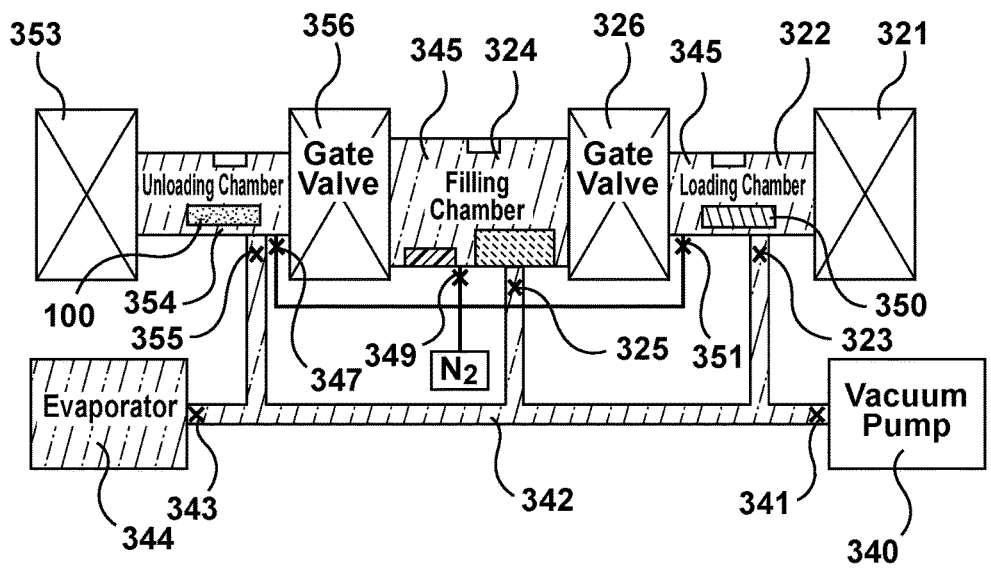
FIG. 32 is a schematic illustration of the apparatus of FIG. 3 being utilized to perform an alternative method of filling multiple batches of stents via capillary action, wherein the loading chamber is saturated with solvent vapor.
Figure 33:
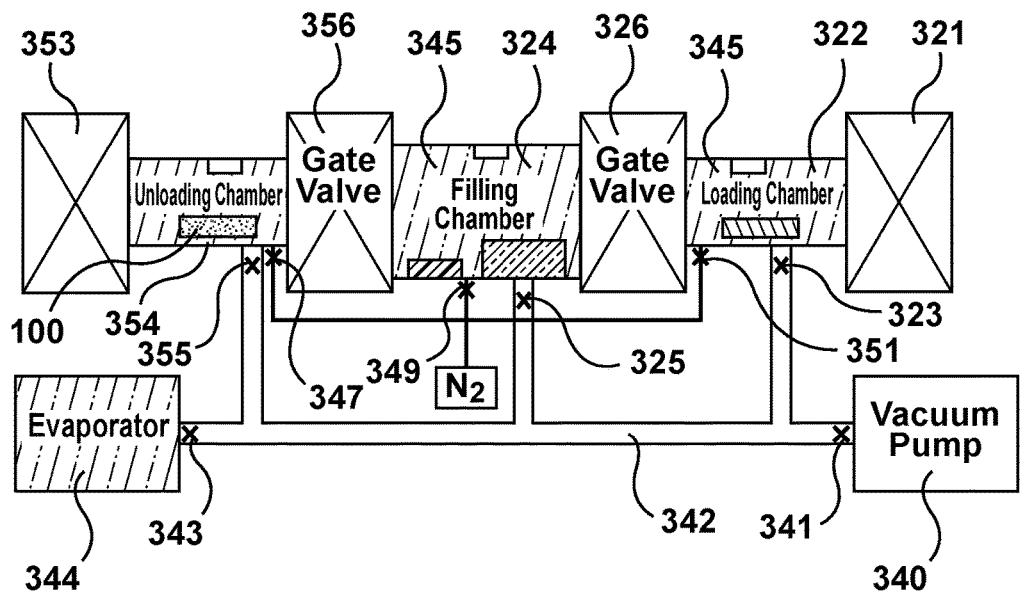
FIG. 33 is a schematic illustration of the apparatus of FIG. 3 being utilized to perform an alternative method of filling multiple batches of stents via capillary action, wherein gas is purged from the network tubing via the vacuum pump.

With reference to FIG. 32, tubing network 342 and loading and unloading chambers 322, 354 are then backfilled with vapor 345 of the solvent of fluid drug formation 334 by opening valve 343 to evaporator 344 which houses a supply of the vapor. Loading and unloading chambers 322, 354 are saturated with vapor 345 of the solvent of fluid drug formation 334 via evaporator 344 such that loading and unloading chambers 322, 354 reach solvent vapor saturation. Stated another way, loading and unloading chambers 322, 354 are at the vapor-liquid equilibrium of the solvent of fluid drug formulation 334. Valves 323, 355 are then closed.

In an embodiment, after backfilling tubing network 342 and loading and unloading chambers 322, 354 with vapor 345 of the solvent of fluid drug formation 334 via evaporator 344, loading and unloading chambers 322, 354 may be backfilled with nitrogen gas 346 by opening valves 351, 347 for stabilization of loading and unloading chambers 322, 354. Adding nitrogen gas 346 to loading and unloading chambers 322, 354 enhances stability and prevents temperature fluctuations within the chamber and system when the loading and unloading chambers are saturated with a vapor of the solvent of fluid drug formulation 334 as described above with respect to FIG. 32. Absolute pressure in loading and unloading chambers 322, 354 is still less than atmospheric pressure at this point in the method. After backfilling loading and unloading chambers 322, 354 with nitrogen gas 346, a dwell or wait time occurs to ensure temperature stabilization of loading and unloading chambers 322, 354. The dwell time may vary between 0.25-15 minutes. Vapor 345 still fills loading and unloading chambers 322, 354, which are sealed off from tubing network 342 as well as filling chamber 324. Gas or residual vapor is purged from tubing network 342 via vacuum pump 340 by opening valve 341.

Figure 34:
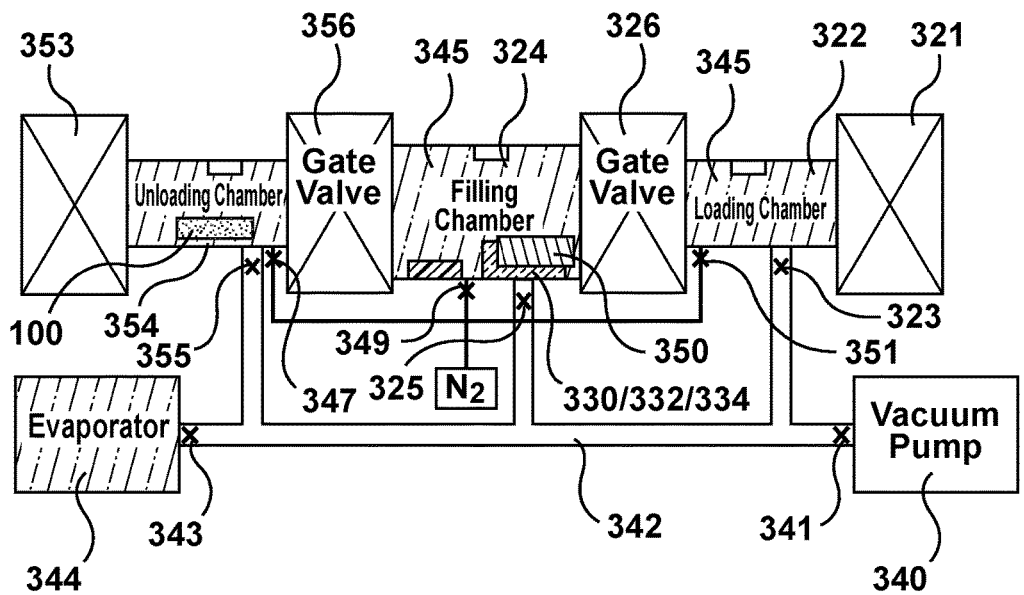
FIG. 34 is a schematic illustration of the apparatus of FIG. 3 being utilized to perform an alternative method of filling multiple batches of stents via capillary action, wherein the stir cover is transferred to the filling chamber and the stir cycle is performed.

Turning now to FIG. 34, with loading and unloading chambers 322, 354 and filling chamber 324 filled with vapor 345, stir cover 350 is transferred into filling chamber 324. More particularly, first valve gate 326 is opened such that filling chamber 324 and loading chamber 322 are in fluid communication. Stir cover 350 is moved or transferred from loading chamber 322 into filling chamber 324 while first valve gate 326 is opened. Stir cover 350 is positioned over reservoir 332, which includes wicking means 330 and fluid drug formulation 334. First valve gate 326 is then closed such that filling chamber 324 and loading chamber 322 are no longer in fluid communication. With stir cover 350 positioned or disposed over reservoir 332, the stir cycle commences and mixes or agitates fluid drug formation 334 and wicking means 330 within reservoir 332 as described above. In another embodiment hereof, first valve gate 326 may remain open during the stir cycle.

Figure 35:
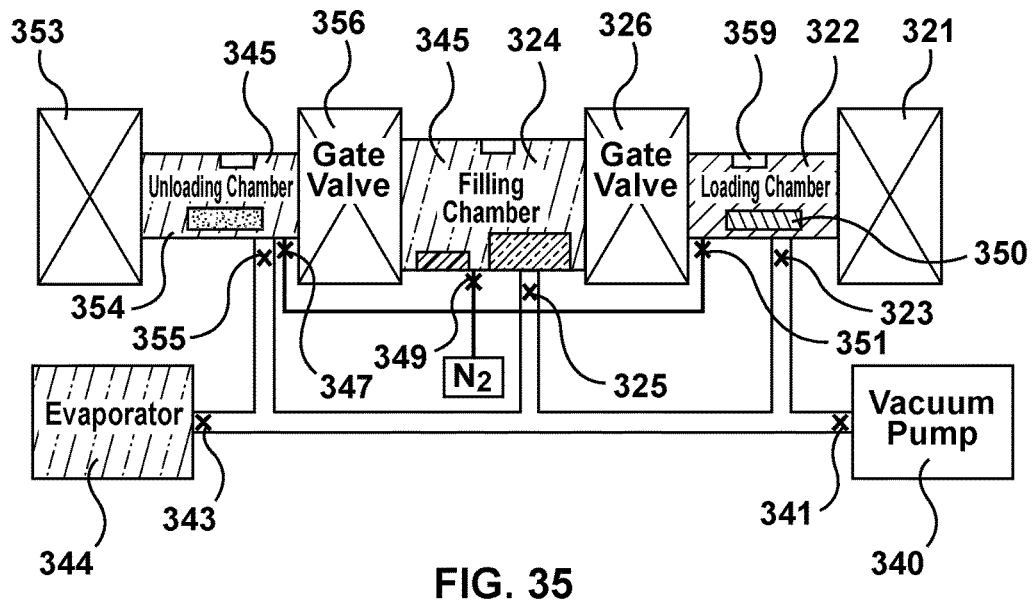
FIG. 35 is a schematic illustration of the apparatus of FIG. 3 being utilized to perform an alternative method of filling multiple batches of stents via capillary action, wherein the stir cover is transferred to the loading chamber and the loading chamber is vented.

With all chambers (loading chamber 322, filling chamber 324, and unloading chamber 354) filled with vapor 345, stir cover 350 is transferred out of filling chamber 324 after the stir cycle is complete as shown in FIG. 35. More particularly, stir cover 350 is moved or transferred from filling chamber 324 into loading chamber 322 while first valve gate 326 is opened. First valve gate 326 is then closed such that filling chamber 324 and loading chamber 322 are no longer in fluid communication. Vapor 345 is then purged from loading chamber 322 via vent 359 and loading chamber 322 returns to atmospheric pressure. In another embodiment hereof, venting may occur via opening valve 351 to backfill loading chamber 322 with nitrogen from the supply of nitrogen gas 346. Stir cover 350 may then be removed from unloading chamber 354 via sealable door 353.

Figure 36:
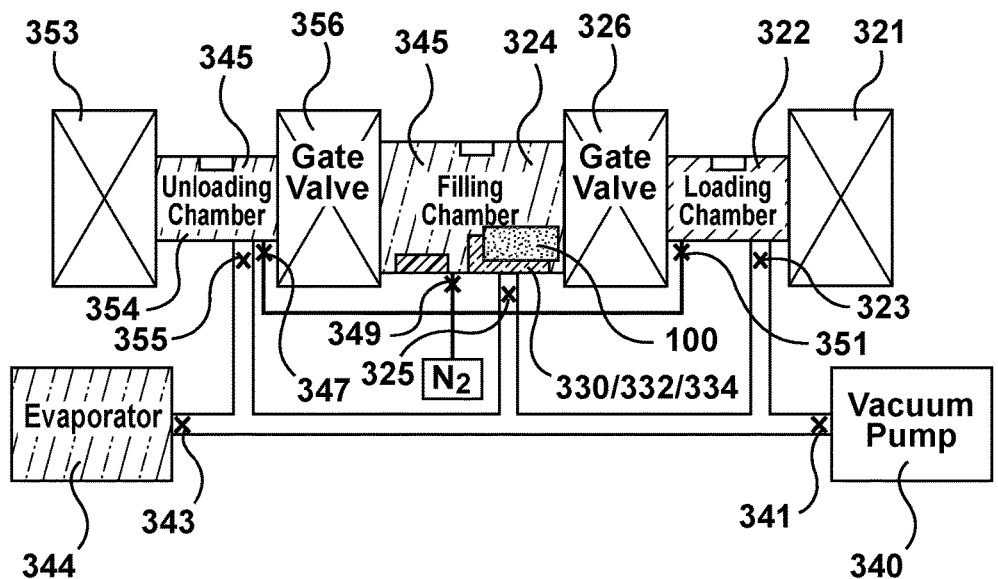
FIG. 36 is a schematic illustration of the apparatus of FIG. 3 being utilized to perform an alternative method of filling multiple batches of stents via capillary action, wherein the first batch of stents is transferred from the unloading chamber into the filling chamber.

FIG. 36 illustrates the fifth step of the alternative method. The fifth step of the alternative method of use is similar to method step 474 described above, and includes transferring the first batch of stents 100 from unloading chamber 354 into filling chamber 324. For sake of completeness a brief description of method step 474 is repeated herein. During this step, valves 323, 325, 355 are closed such that loading, filling, and unloading chambers 322, 324, 354, respectively, are not in fluid communication with tubing network 342. Vapor 345 still fills filling chamber 324 and unloading chamber 354 as shown in FIG. 36. Second valve gate 356 is opened such that filling chamber 324 and unloading chamber 354 are in fluid communication. The first batch of stents 100 are moved or transferred from unloading chamber 354 into filling chamber 324 while second valve gate 356 is opened.

Figure 37:
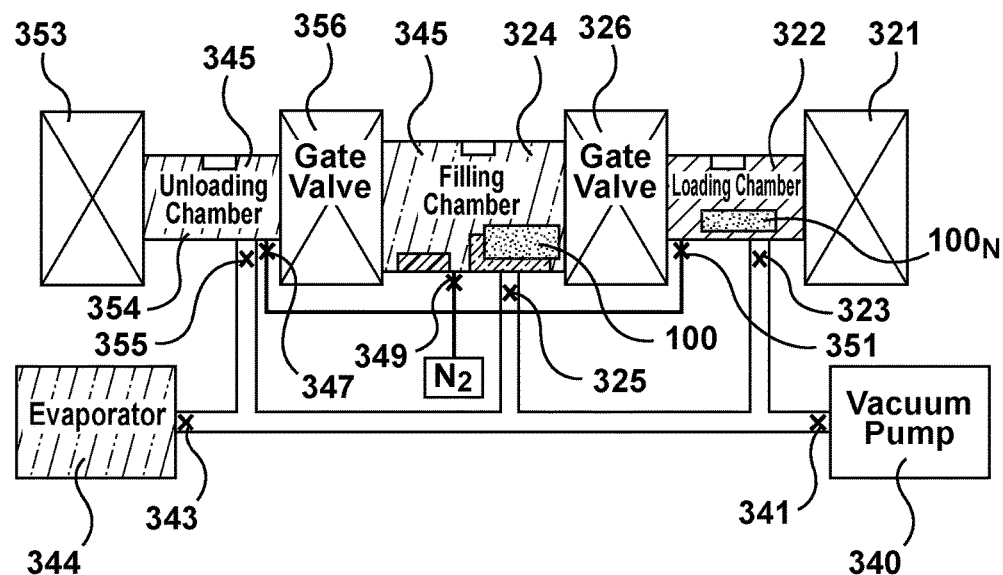
FIG. 37 is a schematic illustration of the apparatus of FIG. 3 being utilized to perform an alternative method of filling multiple batches of stents via capillary action, wherein a second batch of stents is transferred into the loading chamber while the first batch of stents fill via capillary action in the filling chamber.
Figure 38:
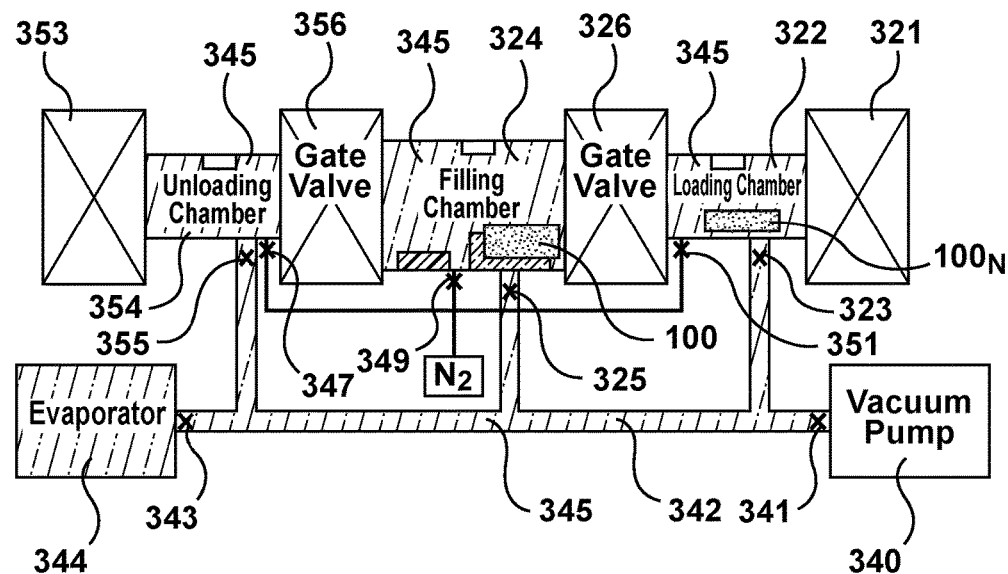
FIG. 38 is a schematic illustration of the apparatus of FIG. 3 being utilized to perform an alternative method of filling multiple batches of stents via capillary action, wherein the loading chamber is saturated with solvent vapor while the first batch of stents fill via capillary action in the filling chamber.
Figure 39:
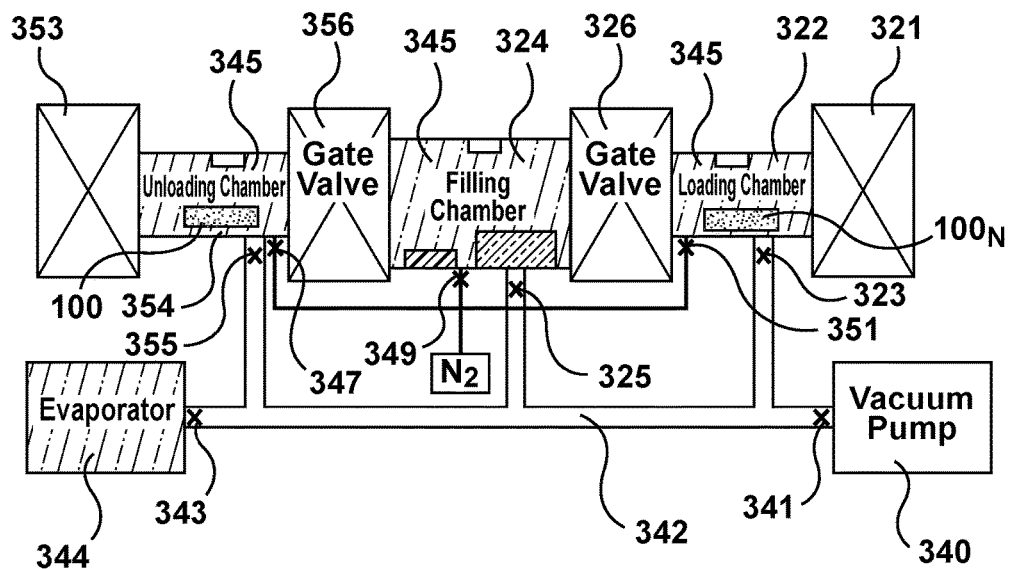
FIG. 39 is a schematic illustration of the apparatus of FIG. 3 being utilized to perform an alternative method of filling multiple batches of stents via capillary action, wherein the first batch of stents is transferred from the filling chamber to the unloading chamber after being filled via capillary action.

FIGS. 37-39 illustrates the sixth step of the alternative method. The sixth step of the alternative method of use is similar to method step 476 described above, and includes filling the first batch of stents 100 via capillary action. However, unlike the previous method, a second batch of stents $100_N$ are positioned or placed into loading chamber 322 while the first batch of stents 100 are being filled in order to increase efficiency of filling multiple, sequential batches of stents in a timely or effective manner. More particularly, with second valve gate 356 still open or closed, the first batch of stents 100 are filled via capillary action while a second batch of stents $100_N$ are positioned or placed into loading chamber 322 as shown in FIG. 37. As described in embodiments above, after the first batch of stents 100 are positioned or placed into contact with wicking means 330, the first batch of stents 100 are allowed or permitted to fill via capillary action. During the filling step, filling chamber 324 and unloading chamber 354 remain in fluid communication and are maintained at or near the vapor-liquid equilibrium of the solvent of fluid drug formulation 334 such that evaporation does not precipitate therapeutic substance or drug 112 as fluid drug formulation 334 fills lumen 103 of hollow wire 102 of the first batch of stents 100.

While filling the first batch of stents 100, loading chamber 322 which holds the second batch of stents $100_N$ is caused to reach the vapor-liquid equilibrium of the solvent of fluid drug formulation 334 in FIG. 38. Valves 323, 341 are opened such that loading chamber 322 is in fluid communication with tubing network 342, but valves 325, 355 remain closed such that filling chamber 324 and unloading chamber 354, respectively, are not in fluid communication with tubing network 342. Gas residuals are purged via vacuum pump 340 to a prescribed set point. Valve 341 is then closed. Tubing network 342 and loading chamber 322 are backfilled with vapor 345 of the solvent of fluid drug formation 334 by opening valve 343 to evaporator 344 which houses a supply of the vapor. Loading chamber 322 is saturated with vapor 345 of the solvent of fluid drug formation 334 via evaporator 344 such that loading chamber 322 reaches solvent vapor saturation. Stated another way, loading chamber 322 is at the vapor-liquid equilibrium of the solvent of fluid drug formulation 334. After loading chamber 322 is sufficiently saturated, valves 323, 343 are closed such that loading chamber 322 and evaporator 344, respectively, are no longer in fluid communication with tubing network 342. In an embodiment, after backfilling loading chamber 322 with vapor 345 of the solvent of fluid drug formation 334 via evaporator 344, loading chamber 322 may be backfilled with nitrogen gas 346 by opening valves 351 for stabilization of loading chamber 322. After backfilling loading chamber 322 with nitrogen gas 346, a dwell or wait time occurs to ensure temperature stabilization of loading chamber 322. The dwell time may vary between 0.25-15 minutes. Vapor 345 still fills loading chamber 322 which is sealed off from tubing network 342, while vapor 345 also still fills both filling chamber 324 and unloading chamber 354. Gas or residual vapor is purged from tubing network 342 via opening valve 341 to vacuum pump 340.

FIG. 39 illustrates the seventh step of the alternative method. The seventh step of the alternative method of use is similar to method step 478 described above, and includes transferring the first batch of stents 100 from filling chamber 345 to unloading chamber 354 via open second gate valve 356 as shown in FIG. 39. After the first batch of stents 100 is positioned within unloading chamber 354, second gate valve 356 is then closed such that filling chamber 324 and unloading chamber 354 are no longer in fluid communication.

Figure 40:
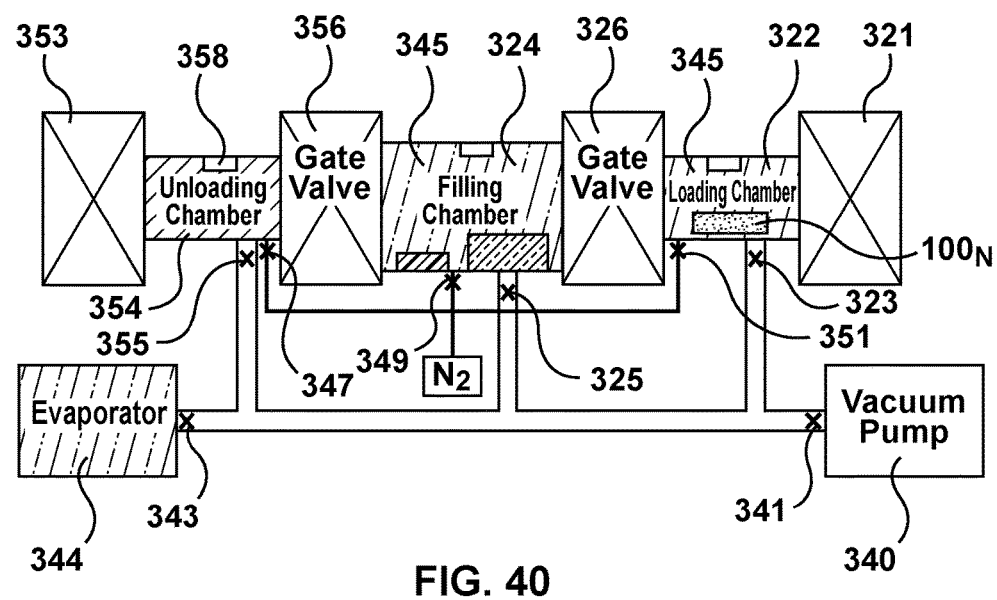
FIG. 40 is a schematic illustration of the apparatus of FIG. 3 being utilized to perform an alternative method of filling multiple batches of stents via capillary action, wherein a therapeutic substance of the fluid drug formulation is precipitated within the lumen of the hollow wire of the first batch of stents and the second batch of stents positioned within the loading chamber is ready to be immediately transferred into the filling chamber for filling via capillary action.

FIG. 40 illustrates the eighth step of the alternative method. The eighth step of the alternative method of use is similar to method step 480 described above, and includes reducing a solvent vapor pressure in unloading chamber 354 to evaporate the solvent of fluid drug formulation 334 after the first batch of stents 100 has been transferred into unloading chamber 354. For sake of completeness a brief description of method step 480 is repeated herein. Vapor 345 still fills filling chamber 324 and loading chamber 322 which holds the second batch of stents $100_N$ as shown in FIG. 40. Vapor 345 is purged from unloading chamber 354 via vents 358 and unloading chamber 354 returns to atmospheric pressure. Stated another way, unloading chamber 354 is vented via vent 358 to both reduce its solvent vapor pressure and return the overall pressure back to ambient conditions. In another embodiment hereof, venting may occur via opening valve 347 to backfill unloading chamber 354 with nitrogen from the supply of nitrogen gas 346. As the solvent vapor pressure is reduced in unloading chamber 354, evaporation is initiated and the solvent of drug fluid formulation 334 is removed, thereby precipitating its constituents. After the solvent or dispersion medium is removed from each lumen 103, therapeutic substance or drug 112 fills at least a portion of each lumen 103 of each stent in the first batch of stents 100. The filled first batch of stents 100 may then be removed from unloading chamber 354 of apparatus 320 (as shown in FIG. 40) and the second batch of stents $100_N$ may be immediately transferred into filling chamber 324 for filling thereof.

In any embodiment hereof, a cleaning step may be utilized after the stent is filled via capillary action to remove excess solid form of the fluid drug formulation or cast film from the exterior surfaces of stents 100. In an embodiment hereof, the additional cleaning step is performed after the stent has been filled with the fluid drug formulation and after the therapeutic drug is precipitated within the lumen of the hollow wire (i.e., after the drying/evaporation step of the process). U.S. Patent Application Publication 2012/0284310 entitled "Apparatus and Methods for Filling a Drug Eluting Medical Device" to Peterson et al., herein incorporated by reference in its entirety, describes several stent cleaning methods that may be utilized herewith. In another embodiment, the additional cleaning step may occur between the filling and drying/evaporation steps of the process and stents 100 may remain in the filling chamber during the cleaning step as described in more detail in U.S. Patent Application Publication 2012/0284310 to Peterson et al., previously incorporated by reference herein. In addition or as an alternative to a cleaning step, at least a portion of the exterior surface of hollow wire 102 of stent 100 may be masked during the filling procedure to prevent the submersed exterior surface from being exposed to the fluid drug formulation. In one embodiment, a monolayer or coating may be applied over at least a portion of stent 100 to mask or cover the exterior surfaces of hollow wire 102 of stent 100 that are to be exposed to a fluid drug formulation, while leaving the drug delivery side ports or openings 104 of stent 100 open so that the fluid drug formulation can fill the lumen of the hollow wire. The monolayer or coating having any excess fluid drug formulation adhered thereto may be removed after the filling process is complete. In an embodiment in which the fluid drug formulation is hydrophilic, the coating is preferably hydrophobic. As the lumenal space of the wire fills, the hydrophilic fluid drug formulation does not stick to the coating or any exposed exterior surfaces of the hollow wire of the stent due to the hydrophobic property of the coating. In another embodiment, as opposed to a coating, a sleeve that slides over hollow wire 102 may be utilized to mask or cover the exterior surfaces of hollow wire 102 of stent 100 that are to be exposed to a fluid drug formulation. Any combination of the aforementioned cleaning and/or masking methods can be employed to clean the stent. The selection of cleaning and/or masking method(s) may be governed by factors such as the drug formulation components and the degree of drug residue after the filling process via capillary action is complete.

Other Applications of Capillary Filling Process

In addition to filling stents formed via a hollow wire for drug delivery, embodiments of the capillary action filling process described above may be applied to other structures. For example, structures having a lumen of a sufficiently small size, such as lumen 103 of hollow wire 102 of stent 100, can be impregnated with any fluid formulation using a capillary action filling process described above. Since only one side opening 104 of the stent is required to be exposed to the fluid formulation, fill weight variation and waste is reduced. In addition to structures having a sufficiently small lumen, structures formed from a porous material, or having a porous material on at least an exterior surface thereof, may be impregnated with any fluid formulation using a capillary action filling process described above. For example, an implantable polyurethane sponge may be impregnated with a fluid drug formulation similar to those described herein for in situ delivery. Other examples include impregnating a wound dressing with antibiotic, impregnating a porous bioabsorbable disc that will be implanted subcutaneously with a fluid drug formulation that suppresses appetite, impregnating a porous bioabsorbable sphere that is to be implanted into a muscle with a fluid drug formulation that encourages muscle growth after atrophy, and impregnating a bioabsorbable stent formed from a porous material with a fluid drug formulation similar to those described herein. Various deformable porous materials that may be impregnated with any fluid formulation using a capillary action filling process described above include porous polymers and hydrogels such as polyurethanes, PEG, PLGA, PLA, PGA, and PE, cotton, silk, TELFA, and cellulose.

Rigid materials, such as metals, ceramics, and rigid polymers, are often utilized as implants and it may be desired to impregnate a rigid material with a fluid drug formulation. Exemplary rigid materials include aluminum, stainless steel, silver, gold, molybdenum, tungsten, tantalum, bronze, ceramics such as borosilicate, hydroxyapatitie, silicon nitride, zirconium dioxide, and polymers such as PET, Polypropylene, HDPE, PVC, polyamides, and fluoropolymers. In order to become porous, rigid materials may undergo processing steps, such as dry etch, a wet or acid etch, application of sintered metal or ceramic powder, application of a metal mesh, or injection of inert gas during liquid metal or polymer solidification. After becoming porous, the rigid materials may then be impregnated with any fluid formulation using a capillary action filling process described above. For example, a hip implant formed from a rigid porous material may be impregnated with a steroid to reduce inflammation after implantation or a spinal screw/plate/rod may be impregnated with an API that encourages bone growth and/or healing.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. For example, FIGS. 30-34 illustrate positioning stents 100 in unloading chamber 354 and stir cover 350 in loading chamber 322 at the same time, and then bringing the loading and unloading chambers to vapor-liquid equilibrium simultaneously. However, in another embodiment hereof (not shown), stir cover 350 may be positioned in loading chamber 322 without positioning of stents 100 in unloading chamber 354 and only loading chamber 322 undergoes the vacuum and vapor backfill steps described above with respect to FIGS. 31 and 32. Stents 100 may then be positioned in unloading chamber 354 at a later time (such as but not limited to after the stir cover is transferred to filling chamber 324 or after the stir cycle) and unloading chamber 354 may undergo vacuum and backfill steps separately to reach the vapor-liquid equilibrium of the solvent of fluid drug formulation 334. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of filling a fluid drug formulation within a lumenal space of a hollow wire that forms a stent, the method comprising the steps of:

causing a filling chamber of an apparatus to reach a vapor-liquid equilibrium of a solvent of the fluid drug formulation, wherein the filling chamber houses a reservoir containing a wicking means and the apparatus includes a valve positioned between the filling chamber and a loading chamber and the valve is closed such that the filling chamber and loading chamber are not in fluid communication;

adding a liquid into a container housed within the filling chamber after the filling chamber has reached the vapor-liquid equilibrium of a solvent of the fluid drug formulation;

adding the fluid drug formulation into the reservoir containing the wicking means after the filling chamber has reached the vapor-liquid equilibrium of a solvent of the fluid drug formulation;

mixing the fluid drug formation and the wicking means within the reservoir;

placing a stent formed from a hollow wire within the loading chamber of the apparatus;

causing the loading chamber of the apparatus to reach the vapor-liquid equilibrium of the solvent of the fluid drug formulation;

opening the valve such that the filling chamber and loading chamber are in fluid communication, wherein the step of opening the valve occurs after both the filling chamber and the loading chamber have reached the vapor-liquid equilibrium of a solvent of the fluid drug formulation;

moving the stent from the loading chamber of the apparatus into the filling chamber of the apparatus while the valve is opened;

closing the valve such that the filling chamber and loading chamber are not in fluid communication after the stent is housed in the filling chamber;

placing at least a portion of the stent into contact with the wicking means within the filling chamber such that the lumenal space of the hollow wire that forms the stent is in fluid contact with the wicking means; and maintaining contact between the wicking means and the stent until a lumenal space defined by the hollow wire is at least partially filled with the fluid drug formulation via capillary action.

2. The method of claim 1, further comprising the steps of:

retracting the stent such that the stent is no longer in contact with the wicking means and is located within the filling chamber;

opening the valve such that the filling chamber and loading chamber are in fluid communication after the stent is retracted;

moving the stent from the filling chamber of the apparatus into the loading chamber of the apparatus while the valve is opened;

closing the valve such that the filling chamber and loading chamber are not in fluid communication after the stent is housed in the loading chamber; and reducing a solvent vapor pressure in the loading chamber to evaporate the solvent of the fluid drug formulation after the valve is closed.

3. The method of claim 2, wherein the step of retracting the stent such that the stent is no longer in contact with the wicking means removes excess fluid drug formulation from an exterior surface of the hollow wire during the step of retracting the stent.

4. The method of claim 2, wherein the step of reducing the solvent vapor pressure in the loading chamber includes venting the loading chamber to ambient pressure.

5. The method of claim 1, wherein the wicking means is a plurality of ceramic beads.

6. The method of claim 1, wherein the steps of causing the filling and loading chambers of the apparatus to reach the vapor-liquid equilibrium of the solvent of the fluid drug formulation include removing gas from the first and loading chambers, respectively, and then backfilling the filling and loading chambers, respectively, with a vapor of the solvent of the fluid drug formulation.

7. The method of claim 1, wherein the step of placing the stent within the loading chamber of the apparatus includes suspending the stent in a horizontal orientation.

8. The method of claim 1, wherein the liquid added into the container of the filling chamber is selected from the group consisting of the solvent of the fluid drug formulation, the fluid drug formulation, or a solution that includes the same solvent as the fluid drug formulation.

9. The method of claim 1, further comprising the step of:

adding a nitrogen gas to the loading chamber after the step of causing the loading chamber of the apparatus to reach the vapor-liquid equilibrium of the solvent of the fluid drug formulation.

10. The method of claim 1, further comprising the steps of:

retracting the stent such that the stent is no longer in contact with the wicking means and is located within the filling chamber, wherein the apparatus further includes an unloading chamber and a second valve positioned between the filling chamber and the unloading chamber, the first and second valves being closed such that the filling chamber, the loading chamber, and the unloading chamber are not in fluid communication;

opening the second valve such that the filling chamber and unloading chamber are in fluid communication after the stent is retracted;

moving the stent from the filling chamber of the apparatus into the unloading chamber of the apparatus while the second valve is opened, wherein the unloading chamber has previously reached and is maintained at the vapor-liquid equilibrium of the solvent of the fluid drug formulation;

closing the second valve such that the filling chamber and unloading chamber are not in fluid communication after the stent is housed in the unloading chamber; and evaporating the solvent of the fluid drug formulation while the stent is housed within the unloading chamber of the apparatus after the second valve is closed.

11. A method of filling a fluid drug formulation within a lumenal space of a hollow wire that forms an implantable medical device, the method comprising the steps of:

causing a filling chamber of an apparatus to reach a vapor-liquid equilibrium of a solvent of the fluid drug formulation, wherein the filling chamber houses a reservoir containing a wicking means and the apparatus includes a valve positioned between the filling chamber and a loading chamber and the valve is closed such that the filling chamber and loading chamber are not in fluid communication;

adding the fluid drug formulation into the reservoir containing the wicking means after the filling chamber has reached the vapor-liquid equilibrium of a solvent of the fluid drug formulation;

placing an implantable medical device formed from a hollow wire within the loading chamber of the apparatus;

transferring the implantable medical device from the loading chamber into the filling chamber by opening the valve such that the filling chamber and loading chamber are in fluid communication, moving the implantable medical device into the filling chamber while the valve is open, and closing the valve such that the filling chamber and loading chamber are no longer in fluid communication after the implantable medical device is housed within the filling chamber;

placing at least a portion of the implantable medical device into contact with the wicking means within the filling chamber such that the lumenal space of the hollow wire that forms the implantable medical device is in fluid contact with the wicking means; and maintaining contact between the wicking means and the implantable medical device until a lumenal space defined by the hollow wire is at least partially filled with the fluid drug formulation via capillary action.

12. The method of claim 11, further comprising the steps of:

retracting the implantable medical device such that the implantable medical device is no longer in contact with the wicking means and is located within the filling chamber;

transferring the implantable medical device from the filling chamber into the loading chamber by opening the valve such that the filling chamber and loading chamber are in fluid communication, moving the implantable medical device into the loading chamber while the valve is open, and closing the valve such that the filling chamber and loading chamber are no longer in fluid communication after the implantable medical device is housed within the loading chamber;

reducing a solvent vapor pressure in the loading chamber to evaporate the solvent of the fluid drug formulation after the implantable medical device is transferred into the loading chamber.

13. The method of claim 12, wherein the step of reducing the solvent vapor pressure in the loading chamber includes venting the loading chamber to ambient pressure.

14. The method of claim 11, wherein the wicking means is a plurality of ceramic beads.

15. The method of claim 11, wherein the step of causing the filling chamber of the apparatus to reach the vapor-liquid equilibrium of the solvent of the fluid drug formulation includes removing gas from the filling chamber and then backfilling the filling chamber with a vapor of the solvent of the fluid drug formulation.

16. The method of claim 11, further comprising the step of:

adding a liquid into a container housed within the filling chamber after the step of causing the filling chamber of the apparatus to reach the vapor-liquid equilibrium of the solvent of the fluid drug formulation and before the step of adding the fluid drug formulation into the reservoir, wherein the liquid added into the container of the filling chamber is selected from the group consisting of the solvent of the fluid drug formulation, the fluid drug formulation, or a solution that includes the same solvent as the drug formulation.

17. The method of claim 11, further comprising the step of:

mixing the fluid drug formation and the wicking means within the reservoir after the step of adding the fluid drug formulation into the reservoir.

18. The method of claim 11, further comprising the step of:

causing the loading chamber of the apparatus to reach the vapor-liquid equilibrium of the solvent of the fluid drug formulation before the step of transferring the implantable medical device from the loading chamber into the filling chamber.

19. The method of claim 18, further comprising the step of:

adding a nitrogen gas to the loading chamber after the step of causing the loading chamber of the apparatus to reach the vapor-liquid equilibrium of the solvent of the fluid drug formulation.

20. The method of claim 11, further comprising the steps of:

retracting the implantable medical device such that the implantable medical device is no longer in contact with the wicking means and is located within the filling chamber, wherein the apparatus further includes an unloading chamber and a second valve positioned between the filling chamber and the unloading chamber, the first and second valves being closed such that the filling chamber, the loading chamber, and the unloading chamber are not in fluid communication;

transferring the implantable medical device from the filling chamber into the unloading chamber by opening the second valve such that the filling chamber and unloading chamber are in fluid communication, moving the implantable medical device into the unloading chamber while the second valve is open, and closing the second valve such that the filling chamber and unloading chamber are no longer in fluid communication after the implantable medical device is housed within the unloading chamber, wherein the unloading chamber has previously reached and is maintained at the vapor-liquid equilibrium of the solvent of the fluid drug formulation;

evaporating the solvent of the fluid drug formulation while the implantable medical device is housed within the unloading chamber of the apparatus.

* * * * *